United States Patent
Matz et al.

(10) Patent No.: US 12,156,707 B2
(45) Date of Patent: Dec. 3, 2024

(54) ASSEMBLY COMPRISING AN OCT DEVICE FOR ASCERTAINING A 3D RECONSTRUCTION OF AN OBJECT REGION VOLUME, COMPUTER PROGRAM, AND COMPUTER-IMPLEMENTED METHOD FOR SAME

(71) Applicant: CARL ZEISS MEDITEC AG, Jena (DE)

(72) Inventors: Holger Matz, Unterschneidheim (DE); Christian Voigt, Abtsgmünd (DE); Christoph Hauger, Aalen (DE); Delbert Peter Andrews, Oberkochen (DE); Nancy Hecker-Denschlag, Ulm (DE)

(73) Assignee: CARL ZEISS MEDITEC AG, Jena (DE)

( * ) Notice: Subject to any disclaimer, the term of this patent is extended or adjusted under 35 U.S.C. 154(b) by 160 days.

(21) Appl. No.: 17/793,800

(22) PCT Filed: Jan. 25, 2021

(86) PCT No.: PCT/EP2021/051642
§ 371 (c)(1),
(2) Date: Jul. 19, 2022

(87) PCT Pub. No.: WO2021/151841
PCT Pub. Date: Aug. 5, 2021

(65) Prior Publication Data
US 2023/0053366 A1    Feb. 23, 2023

(30) Foreign Application Priority Data
Jan. 28, 2020 (DE) ............... 10 2020 102 012.0

(51) Int. Cl.
*A61B 34/20* (2016.01)
*A61B 3/10* (2006.01)
(Continued)

(52) U.S. Cl.
CPC .............. *A61B 34/20* (2016.02); *A61B 3/102* (2013.01); *A61B 3/1225* (2013.01); *A61B 34/10* (2016.02);
(Continued)

(58) Field of Classification Search
CPC ....... A61B 34/20; A61B 3/102; A61B 3/1225; A61B 34/10; A61B 2034/107;
(Continued)

(56) References Cited

U.S. PATENT DOCUMENTS

| 2012/0190976 A1 | 7/2012 | Kleinstreuer | |
| 2014/0206940 A1* | 7/2014 | Hufford | ............. A61B 17/3203 604/521 |

(Continued)

FOREIGN PATENT DOCUMENTS

| EP | 2949284 A1 | 12/2015 |
| EP | 3005937 A1 | 4/2016 |
| EP | 3461411 A1 | 4/2019 |

OTHER PUBLICATIONS

International Search Report for Application No. PCT/EP2021/051642, mailed May 11, 2021, (8 pages).
(Continued)

*Primary Examiner* — Rochelle D Turchen
(74) *Attorney, Agent, or Firm* — NIXON PEABODY LLP; Jeffrey L. Costellia

(57) ABSTRACT

The invention relates to an arrangement 10 with an OCT device 20 for scanning an object region volume 22 arranged in an object region 18 with an OCT scanning beam 21, comprising an item 24 which has a section 84 that is
(Continued)

arrangeable in the object region 18 and is localizable in the object region volume 22 by means of the OCT device 20, and having a computing unit 60 connected to the OCT device 20 and having a computer program for determining a 3-D reconstruction of the object region volume 22 and determining the location of the portion of the object 24 in the object region volume 22 by processing OCT scan information obtained with the OCT device 20 by scanning the object region volume 22. According to the invention, the computer program has a calculation routine for determining a target area in the 3-D reconstruction of the object region volume 22, which routine determines a reference variable for the object 24 for the target area. The computer program contains a path planning routine that uses a criterion to calculate an optimal path for object 24 to the target spatial position, the criterion being a shadow measure that quantifies the occurrence of shadows caused by object 24 in the calculated 3-D reconstruction. The invention also relates to a computer program and a method for determining a 3-D reconstruction of an object region volume 22 in an object region 18.

15 Claims, 10 Drawing Sheets

(51) Int. Cl.

| | | |
|---|---|---|
| *A61B 3/12* | (2006.01) | |
| *A61B 34/10* | (2016.01) | |
| *A61B 90/00* | (2016.01) | |
| *A61F 9/00* | (2006.01) | |
| *A61F 9/007* | (2006.01) | |
| *G06T 7/11* | (2017.01) | |
| *G06T 7/30* | (2017.01) | |
| *G06T 11/00* | (2006.01) | |

(52) U.S. Cl.
CPC ............ *A61B 90/39* (2016.02); *A61F 9/0017* (2013.01); *A61F 9/007* (2013.01); *G06T 7/11* (2017.01); *G06T 7/30* (2017.01); *G06T 11/003* (2013.01); *A61B 2034/107* (2016.02); *A61B 2034/2065* (2016.02); *A61B 2090/3937* (2016.02); *G06T 2207/10101* (2013.01); *G06T 2207/30041* (2013.01); *G06T 2207/30204* (2013.01)

(58) Field of Classification Search
CPC ..... A61B 2034/2065; A61B 2090/3937; A61F 9/0017; A61F 9/007; G06T 7/11; G06T 7/30; G06T 11/003; G06T 2207/10101; G06T 2207/30041; G06T 2207/30204
See application file for complete search history.

(56) References Cited

U.S. PATENT DOCUMENTS

| | | | |
|---|---|---|---|
| 2016/0089015 A1* | 3/2016 | Eslami | ...................... G06T 5/50 351/206 |
| 2016/0249989 A1 | 9/2016 | Devam et al. | |
| 2016/0335766 A1* | 11/2016 | Ambwani | .................. G06T 7/11 |
| 2017/0209042 A1 | 7/2017 | Matz et al. | |
| 2018/0070818 A1 | 3/2018 | Sakai | |
| 2018/0263706 A1 | 9/2018 | Averbuch | |
| 2019/0000563 A1 | 1/2019 | Scheider et al. | |

OTHER PUBLICATIONS

German Office Action for Application No. 102020102012.0, mailed Nov. 12, 2020, (18 pages).
Written Opinion for Application No. PCT/EP2021/051642, mailed May 11, 2021, (14 pages).

* cited by examiner

ASSEMBLY COMPRISING AN OCT DEVICE FOR ASCERTAINING A 3D RECONSTRUCTION OF AN OBJECT REGION VOLUME, COMPUTER PROGRAM, AND COMPUTER-IMPLEMENTED METHOD FOR SAME

CROSS-REFERENCE TO RELATED APPLICATIONS

The present application is the U.S. national stage entry of International Application No. PCT/EP2021/051642, filed Jan. 25, 2021, which claims the benefit of and priority to German Patent Application No. 10 2020 102 012.0, filed Jan. 28, 2020, the contents of which are incorporated by reference herein in their entirety.

The invention relates to an arrangement comprising an OCT device for scanning an object region volume in an object region by means of an OCT scanning beam and comprising an item which has a section that is arrangeable in the object region volume and is localizable there by means of the OCT device, and comprising a computer unit which is connected to the OCT device and which contains a computer program for determining a 3-D reconstruction of the object region volume and determining the relative position of the section of the item in the object region volume by processing scanning information obtained by means of the OCT device by scanning the object region volume. The invention also relates to a computer program and a computer-implemented method for determining a 3-D reconstruction of an object region volume.

Optical coherence tomography (OCT) is a method for acquiring volume data, in particular of biological tissue, by scanning the tissue by means of an OCT scanning beam made of temporally incoherent but spatially coherent laser light, which is guided in a sample beam path and a reference beam path. OCT allows the localization of objects such as, e.g., surgical objects in an operating region.

WO 2016 055422 A1 and US 2017/0209042 A1 each have disclosed an arrangement of the type set forth at the outset. These documents describe a surgical system comprising an OCT device and comprising a surgical instrument, which has an effective section that is localizable by means of the OCT device. These state that a target area should be determined for the surgical instrument from reference data and an offset of the surgical instrument in relation to the target area should be used as a criterion for triggering an instrument function.

US 2019/0000563 A1 describes a system for determining a relative position and orientation of an instrument tip during ophthalmological surgery. In this case, the tissue of the eye is detected by means of OCT, in particular, and the relative position and orientation of the instrument tip is determined by means of image capture, by means of magnetic sensors, by means of ultrasound sensors or by means of inertial sensors in a coordinate system referenced to the detected tissue on the basis of a marker attached to the instrument.

US 2016/0249989 A1 discloses a visualization system which, on the body of a patient, can render visible virtual structures referenced in relation thereto.

EP 3 461 411 A1 has disclosed the processing of the OCT data over various object regions to form a model by virtue of referencing OCT data in relation to the different object regions.

US 2018/0263706 A1 teaches the processing of patient images which contain shadow structures and which were captured by means of the transillumination.

US 2012/0190976 A1 describes the controlled release of active substances using a micro-catheter that has been introduced into the blood circuit of a patient, by virtue of the pressure in an active substance reservoir being determined by means of a pressure sensor and the active substance flow out of the active substance reservoir being controlled by way of a micro-valve.

It is an object the invention to simplify surgical interventions for a surgeon in an operating region that is difficult to access.

This object is achieved by the arrangement specified in claim 1, the computer program specified in claim 14, and the method specified in claim 15. Advantageous embodiments of the invention are specified in the dependent claims.

The arrangement specified in claim 1 comprises an OCT device for scanning an object region volume arranged in an object region using an OCT scanning beam, and an item which has in the object region volume a section that is arrangeable in the object region and is localizable in the object region volume by means of the OCT device. Moreover, the arrangement contains a computer unit which is connected to the OCT device and which has a computer program for determining a 3-D reconstruction of the object region volume and determining the relative position of the section of the item in the object region volume by processing OCT scanning information obtained by the OCT device by scanning the object region volume. In this case, the computer program has a computing routine for determining a target area in the 3-D reconstruction of the object region volume, said computing routine determining a guide variable for the item in relation to the target area. The computer program contains a path planning routine which calculates an optimal path of the item to the spatial target position on the basis of a criterion. In this case, the criterion is a measure of shadowing that quantifies the presence of shadows caused by the item in the calculated 3-D reconstruction.

An OCT device in an arrangement according to the invention comprises a source for temporally incoherent and spatially coherent laser light with a coherence length lc, which is fed to a sample beam path and a reference beam path. The sample beam path is directed at the tissue to be examined. The laser light which is radiated back into the sample beam path on account of scattering centers in the tissue has laser light from the reference beam path superposed thereon in the OCT device. An interference signal arises as a result of this superposition. The position of scattering centers for the laser radiation in the examined tissue may be determined from this interference signal. In particular, an OCT device in a surgical system according to the invention may be designed as a "time domain OCT" or as a "Fourier domain OCT".

The path planning routine facilitates improvements in the automation of the surgical method and in the accuracy of the item guidance while at the same time increasing the flexibility for the surgeon.

By virtue of minimizing the measure of shadowing for the item or by virtue of not exceeding a specified threshold, it is possible to avoid shadowing in the data from the outset. By way of example, if the light source position and position and orientation of the item in the object region are known, the measure of shadowing can calculate, in advance, the region in the data shadowed by the item and the magnitude of the shadowing for a certain path of the item to the target position in the target area.

In this case, it is advantageous if the computer program contains a visualization routine for visualizing an optimal path of the item for a surgeon. As a result, said surgeon can verify the path of an item even before the movement of the latter and can implement a corrective intervention when necessary.

In an advantageous embodiment of the invention, the surgeon can specify the criterion for the path planning routine so that they can themselves directly influence the automatic implementation of the operation by selecting the criterion.

In this case, the criterion may also in particular minimize path lengths of paths along which an item is displaced; it can protect sensitive regions of the object region volume by virtue of observing a minimum distance of the items from these regions when planning the path, or it can avoid shadowing in the data as a result of these items. As a result of formulating an optimization problem with a target function to be optimized, it is also possible to simultaneously consider a plurality of criteria within the scope of path planning. In this case, these criteria can be included in the target function, in each case weighted by their relevance.

In particular the injection of stem cells into the retinal tissue for treating what is known as dry macular degeneration (AMD) facilitates the reduction in the drusen reformation and allows already damaged retinal pigment epithelium and damaged photoreceptors to heal again. However, what is essential here is that the stem cells injected into the retinal tissue are released by a surgeon at the right location and in the right amount. Exact positioning is also important for the placement of implants on the retina, for example for the placement of what are known as nano retinal implants. Moreover, it is important for some operations to remove the vitreous humor as exactly as possible in the run-up thereto.

In particular, a localization that is as exact as possible of items such as, for instance, surgical instruments, implants but also tissue is therefore desirable for the success of such an operation.

In the present case, the term 3-D reconstruction denotes the process of capturing the shape and the appearance of real objects or parts thereof. By way of example, the 3-D reconstruction can be available as a depth map, a point cloud or a mesh. The process can be carried out using active or passive techniques. Active techniques actively interact with the object to be reconstructed in mechanical or radiometric fashion using distance measuring devices. By contrast, passive techniques only use a sensor in order to measure the radiation reflected or emitted by the surface of the object and use this to deduce the 3-D structure of said object by way of image understanding.

This invention understands a target area to be a portion in the 3-D reconstruction of the object region volume, in which the item should be brought to bear by virtue of a function of the item being carried out or by virtue of the item being placed there. To this end, this portion can contain a target position.

Determining the target area in the 3-D reconstruction of the object region volume and determining the guide variable for the item by the computer program facilitate an automation of the guidance of surgical instruments and further items during the operation.

The invention understands a guide variable to be a variable which is determined by the computer program and which serves to guide an item in the object region. Here, such a variable denotes a quantitatively determinable property of a procedure or state when guiding the item. The guide variable can directly describe the guiding of the item, for example in the form of a direction, a speed, a position or a temporal extent. The guide variable can also describe the guiding of the item indirectly, for example in the form of an amount, a volume or a spatial extent of a medium which should be released into or removed from the object region by means of the item. Here, the guide variable is advantageously determined by processing data of the target area.

The item can be a surgical instrument in particular and the section of the item can be an effective section of the surgical instrument.

It is advantageous if a marker that is localizable by means of the OCT scanning beam is arranged in the section of the item and/or in the object region. This makes it easy to determine the relative position of the item in the object region volume and/or to determine the 3-D reconstruction and thereby contributes to the automation of the surgical method.

Preferably, the computer program contains a routine for generating a guide variable in the form of control signals for the item, in particular a surgical instrument. Alternatively, the computer program can generate control signals for the item on the basis of a guide variable determined in relation to the target area. These measures allow automation of the guidance of the item. Moreover, the accuracy of the item guidance can be improved, leading to increased chances of success of the surgery and to lower risks of complications, for example as a result of injury to vessels or hand tremors of the surgeon.

In a preferred embodiment, the item is in the form of a surgical instrument which has a capillary with an opening for the release of a medium. By way of example, the surgical instrument in this case is an injection needle for injecting stem cells for the treatment of AMD, which can be performed in automated fashion to the greatest possible extent on the basis of the arrangement according to the invention and the computer program.

Further preferably, the computing routine of the computer program serves to determine as a guide variable a target value for the volume of the released medium by processing the target area in the 3-D reconstruction of the object region volume and/or by processing data determined presurgery and/or by processing OCT scanning information obtained by means of the OCT device by scanning the object region volume and/or by way of an input of a target value by a surgeon. The target value for the volume of the released medium can be determined, for example, by means of image processing from the specified data or a combination of these data. This measure is advantageous in that the determination of the target value can be automatically undertaken directly by the computer program. When using the 3-D reconstruction or OCT scanning information, this additionally has the advantage that the target value is adapted to the conditions currently present in the object region of the patient and is not adapted to data which are recorded at an earlier time.

Advantageously, the computing routine of the computer program serves to determine an actual value of the volume of the medium released into the target area by comparing data of the target area in the 3-D reconstruction of the object region volume and/or scanning information of the target area obtained by means of the OCT device by scanning the object region volume before and during the release of the medium. In this case, the actual value of the volume of the medium released in the target area can be determined by means of image processing. Moreover, the change in the volume can be determined by evaluating difference images which arise as the difference of OCT data captured at different times and/or of 3-D reconstructions determined at different times. On the basis of the difference images it is moreover possible to deduce the position of leaks possibly present.

The computing routine of the computer program is advantageously designed to determine as a guide variable for a readjustment of the volume of the released medium a difference between a target value and an actual value of the volume of the medium released into the target area. As a result, the volume of the amount of medium still to be released into the target area from the surgical instrument is determined automatically. This facilitates an automatic readjustment of the volume of the released medium on the basis of the data of the target area present. These measures consider leakages possibly present and ensure that the specified volume of medium is in fact also applied to the target area. If necessary, the target area or a target position in the target area can be adjusted while the medium is released.

On the basis of the determined guide variable for readjusting the volume of the released medium, the computer program can generate control signals for the surgical instrument for releasing the medium and/or a volume-indication signal for a surgeon.

A further preferred embodiment of the invention relates to the removal of substances from the determined target area in the 3-D reconstruction of the object region. By way of example, the substance can be tissue, water or vitreous humor. In this case, the computing routine of the computer program serves to determine as a guide variable the position of the substance to be removed and/or the amount of substance to be removed by processing the target area in the 3-D reconstruction of the object region volume and/or by processing data determined presurgery and/or by processing scanning information obtained by means of the OCT device by scanning the object region volume and/or by way of an input of a target value by a surgeon. In this case, positions in the object region volume where a substance to be removed still is present can be determined by means of an image processing of the target area in the given data. Alternatively, the volume of the substance still to be removed can also be determined for a given position. On the basis of these guide variables it is then possible to generate control signals for the automatic displacement of the item in the object region to the substance still to be removed.

To allow a full removal of the substance to be removed, this substance can be rendered identifiable by the injection of a marker, in particular triamcinolone. This allows the substance to be removed with a greater accuracy. This increases the chances of success of the operation and protects surrounding vessels.

Advantageously, the computer program has a visualization routine for visualizing the position of the substance to be removed and/or an amount of substance to be removed in the object region volume. To this end, it is possible for example to augment the 3-D reconstruction by virtue of marking the positions. Alternatively, it is also possible to present a contour map in relation to the target area of the object region volume, in which the amount of substance to be removed is specified as a height at various positions. Alternatively, it is possible to present a display bar indicating the amount of substance still to be removed for the current position of the item in the object region volume.

By way of example, the substance can be material of a vitreous humor. Vitreous humor removal is carried out using an item, for example a vitrectome. An exact vitrectomy without remains is important for the success of retinal implant surgery, as it facilitates an improved signal-to-noise ratio. In this case, the vitreous humor to be removed is visualized to the surgeon on the basis of a contour map which indicates for each point on the retina the amount of the vitreous humor, located thereabove, to be removed. In this case, the computer program is advantageously designed to continuously determine the boundary between vitreous humor and a solution for rinsing the operating region within the scope of the vitrectomy and/or display said boundary to the surgeon. This measure is advantageous in that the boundary between vitreous humor and the solution for rinsing the operating region can be clearly highlighted in a visualization of the operating region. The automated detection of the vitreous humor remains by means of segmentation facilitates the measurement of the remaining thickness of the layer. The vitreous humor remains can then be displayed to a surgeon in each visualization of the operating region, simplifying the implementation of the surgery and reducing the risk to the patient.

In a further advantageous embodiment, the item is in the form of an implant.

Furthermore, it is advantageous that the computer program is designed to determine as a guide variable a spatial target position in the target area in the 3-D reconstruction of the object region volume taking account of characteristic features of the item and/or of a further item and/or of the target area in the 3-D reconstruction of the object region volume, and/or taking account of geometric relationships, in particular offset information, between these. In this case, characteristic features denote in particular dimensions, for example of the implant or of portions of the implant, but also dimensions of the further item, for example in the form of a surgical instrument, or of regions of the target area. Characteristic features may also describe structures thereof, for example a 3-D electrode on the back side of the item in the form of an implant, or the course of blood vessels in the object region volume. Geometric relations describe in particular the relative positions of regions with respect to one another, for example the distance of an item from a blood vessel in the object region volume. Taking account of characteristic features and/or geometric relations when determining the guide variable by way of the computer program is advantageous in that the attachment of the item in the object region volume can be carried out automatically and also with greater accuracy and with the lowest possible risk of complication. Advantageously, the seat of the item is verified after attaching said item, for example an implant, in its target area.

Preferably, OCT angiography data of the object region volume are generated in all embodiments from the scanning information obtained by means of the OCT device by scanning the object region volume. OCT angiography is a clinical examination method that allows a noninvasive three-dimensional representation of the vascular structures of the retina and choroid. From a technical point of view, OCT-A is a development of optical coherence tomography (OCT). As a result of more powerful software and hardware, OCT-A facilitates not only morphological analyses but also a three-dimensional retinal and choroidal perfusion analysis. In this case, the computer program is advantageously designed for determining the position and/or the dimensions of blood vessels in the target area on the basis of the OCT angiography data. The representation and/or measurement of blood vessels in the target area by means of OCT-A is advantageous in that the position and/or the dimensions of the blood vessels are taken into account by the computing routine of the computer program, which determines a guide variable for the item in relation to the target area, when guiding and placing items and when determining the target area or target positions within the latter. This avoids complications as a result of injury to relatively large blood vessels during the intervention.

In particular, it is advantageous here if the computer program has a position calculation routine for determining a spatial target position in the target area for the item, which position calculation routine is designed to minimize the number of blood vessels punctured when placing the item at the spatial target position. This measure also minimizes the probability within the operation of injuring relatively large blood vessels or a greater number of blood vessels than necessary.

An advantageous embodiment of the invention contains a device for visualizing the relative position of the section of the item in the 3-D reconstruction of the object region volume and/or of data determined presurgery and/or the guide variable to be determined in relation to the target area and/or variables derived from this guide variable. As a result, a surgeon can permanently monitor the relative position of the items, e.g., of implants or surgical instruments, within the 3-D reconstruction of the object region volume. Data determined presurgery can likewise be visualized in order to display to the surgeon, e.g., the target area determined presurgery or further information planned prior to surgery. Ascertained guide variables such as control signals for displacing the items and amounts of a volume to be released or of a substance to be removed can also be visualized for the surgeon. This also applies to variables derived from a guide variable, for example a volume to be readjusted, which is determined from a previously determined guide variable in the form of a target value for the volume to be released. The computer program can generate acoustic, optical or haptic indication signals for the surgeon on the basis of the guide variable determined in relation to the target area and/or variables derived therefrom.

An advantageous development of the invention provides for the computer program to contain a shadowing routine for determining a corrected 3-D reconstruction of the object region volume, said shadowing routine recognizing regions that are shadowed by the item and specifying a compensation rule for the 3-D reconstruction of the object region volume in relation to these regions. As a result, it is possible to determine a corrected 3-D reconstruction of the object region volume without shadowing which reduces the visibility of the details in individual regions. This ensures a better manageability of the arrangement for the surgeon as a result of an improved 3-D impression of the object region volume, and greater accuracy in the data of the target positions and/or target areas to be determined. This also reduces the risk of complications during the operation since important regions in the data are not covered by shadows.

In this case, the shadowing routine for recognizing the regions shadowed by the item and/or for specifying the compensation rule for the 3-D reconstruction may use OCT data from different recording times, as described in EP 3 005 937 A1. As an alternative thereto, the shadowing routine for recognizing shadowed regions and/or for specifying the compensation rule may use data from other modalities, for example optical data, MRI data, ultrasound images or CT data. By way of example, shadows may be more easily recognizable in these data than in OCT data, or these data may even be shadowless. Data 92 determined presurgery may also be used to this end. Alternatively, the shadowing routine for the recognition and replacement of shadows may also take account of the currently calculated 3-D reconstruction 94 and/or the currently recorded OCT data.

To recognize the shadowed regions it is possible, for example, to analyze grayscale values of the acquired OCT data and compare these to the grayscale values in the surroundings or at different times. By defining a threshold, it is possible to identify points with grayscale values below the threshold to be shadows. To recognize shadows it is also possible to consider the profile of edges in the images. A long, straight edge in this case indicates a shadow of an artificial item since long straight edges normally do not occur in the tissue of the body. Alternatively, if the positions of the light source and of the item are known during the operation, it is also possible to calculate the position of a shadow by means of ray tracing.

Alternatively, the shadowing routine can replace regions shadowed by the item in the 3-D reconstruction of the object region volume using data relating to the shadowed regions, which were acquired at the same time at locations away from the shadow of an element. Alternatively, the shadowing routine can replace regions shadowed by the item with data generated by the computer program, for example by means of inpainting methods as described in the document "Liu, Yaojie and Shu, Chang, A comparison of image inpainting techniques, Proceedings of SPIE—The International Society for Optical Engineering, 2015", the entirety of which is referenced herewith and the disclosure of which is incorporated in the description of this invention. These measures are advantageous in that information within the shadowed regions can be represented as realistically as possible, contributing to the safety of the patient. Moreover, these facilitate a representation of the 3-D reconstruction without bothersome element shadows, which representation is easy to implement and requires little computation time.

An advantageous development of the invention provides for the computer program to be designed to determine a spatial target position for the item in the 3-D reconstruction of the object region volume. Preferably, the spatial target position for the item is determined here in the target area within the object region volume. This measure contributes to an automation of the surgical method and to a greater accuracy when guiding the item.

It is advantageous for the computer program to be designed to determine offset information about the spatial offset of the section of the item from the spatial target position. On the basis of the offset information the computer program is able to automatically generate control signals for guiding the item such that this measure also assists the automation of the surgical method and the accuracy of the item guidance.

An advantageous embodiment of the invention provides for the computer program to be designed to determine a 3-D reconstruction of the object region volume from data which are obtained by examining the object region volume using an imaging method, in particular by scanning the object region volume by means of the OCT scanning beam of the OCT device, and/or which are data determined presurgery and/or which are data relating to sensor signals for determining a position of the section of the item in the object region volume. In this case, a person skilled in the art can use conventional methods for calculating the 3-D reconstruction of the object region volume, for example as described in the publication "Justin A. Eichel, Kostadinka K. Bizheva, David A. Clausi, Paul W. Fieguth, Automated 3D Reconstruction and Segmentation from Optical Coherence Tomography, Proceedings of the European Conference on Computer Vision (ECCV), 2010, p. 44-57", or simultaneous localization and mapping methods (SLAM), for example as described in the publication "Hugh Durrant-Whyte, Tim Bailey, Simultaneous Localization and Mapping (SLAM): Part I The Essential Algorithms, Robotics and Automation Magazine, 2006". The entirety of both aforementioned publications is referenced herewith and the disclosure of which is incorporated in the description of this invention. This measure is advantageous in that the calculated 3-D reconstruction can be carried out with the greatest possible accuracy, and so the result is as realistic as possible. This increases the safety of the patient.

It is also advantageous if the computer program is designed to determine the relative spatial position of data by means of a registration method, said data comprising data from the following group: scanning information obtained by means of the OCT device by scanning the object region volume, the object region volume, data from further imaging methods, in particular optical image representations, MRI data, CT data, ultrasound images, endoscopy images, a position of the section of the item, data determined presurgery, position sensor signals. By using different types of data it is possible to take account of and/or represent different aspects of the target area in the object region volume. Moreover, the use of redundant information in data from different modalities leads to greater accuracy of the result of the registration method.

For registration methods, use can be made of methods known to a person skilled in the art, in particular methods for registering medical data, as are found in the publication "F. Oliveira, J. Tavares, Medical Image Registration: a Review, Computer Methods in Biomechanics and Biomedical Engineering, 2014", for example, the entirety of which is referenced herewith and the disclosure of which is incorporated in the description of this invention.

It is furthermore advantageous if the computer program is designed for successive registration of the data. As a result, the result of the registration is always matched to the currently present conditions, increasing the safety of the patient.

Preferably, the generation of the OCT data and the calculation of the 3-D reconstruction and the registration of the various data are implemented in real time in this case in order to facilitate a visualization of the item in the current object region volume for the surgeon in real time such that the surgeon can verify the course of the operation at all times. This measure also improves the safety of the patient.

In an advantageous development of the method, the OCT device is designed for successive continuous scanning of the object region volume by means of the OCT scanning beam and/or the OCT device is designed for successive continuous scanning of a region of the object region volume containing the section of the item by means of the OCT scanning beam. It is also advantageous if the computer program is designed for successive continuous determination of the 3-D reconstruction of the object region volume and/or for successive continuous determination of the relative position of the section of the item in the object region volume. This is because the OCT scanning information and the 3-D reconstruction of the object region volume generated from these data and the relative position of the item in the object region is always adapted to the currently present conditions as a result, increasing the manageability of the system and the safety of the patient. In particular, it is advantageous here if the OCT scanning information and the determination of the 3-D reconstruction and the relative position of the section of the item in the object region volume are implemented in real time.

It is advantageous if the computer program contains a scanning routine for scanning the object region volume and/or the section of the item using specific scanning patterns and/or for adjusting a scanning rate, which scans the object region volume at a lower rate in comparison with the position of the section of the item. This ensures that the quickly changing regions, in particular the item, are scanned at a higher rate than the regions which normally change only slowly. This measure saves computing time and leads to greater accuracy of the determined relative position of the item.

The provision during surgery of data determined presurgery from a memory connected to the computer unit is advantageous. In this case, the data determined presurgery may originate from the group comprising images of the object region, in particular further regions of sections of the object region, images or data of a target area, distances, target positions, geometric data of the item, in particular its dimensions or material properties such as reflection properties for example, sensor signals, biometric patient data, in particular biometric data such as the pupil size or the distance between the eyes. The computer program contains a routine for determining a target area and/or a target position for the item in the data determined presurgery and a registration routine for registering the data determined presurgery with the 3-D reconstruction of the object region volume and a transfer routine for transferring the target area and/or the target position in the data determined presurgery to the 3-D reconstruction of the object region volume. As a result, it is possible to automatically transfer information items such as target areas and/or target positions from the data determined presurgery to the 3-D reconstruction present. This facilitates comprehensive automation of the surgical method and an accurate localization of the target area and/or the target position in the 3-D reconstruction on the basis of the presurgical data.

It is moreover advantageous if the computer program is designed to determine target areas and/or spatial target positions in the data determined presurgery or in the 3-D reconstruction of the object region volume by virtue of applying methods for segmenting tissue structures and/or tissue layers. This measure contributes to a higher degree of automation of the surgical method.

It is advantageous if the computer program is designed to adapt the method for calculating the 3-D reconstruction and/or the method for calculating the relative position of the section of the item in the object region volume on the basis of a criterion. It is further advantageous in this case if the method is adapted continuously during surgery. Preferably, the criterion takes properties of the data and/or of the object region and/or of the item and/or of the arrangement and/or of the registration method and/or of the currently calculated 3-D reconstruction and/or of the currently calculated relative position of the section of the item into account during this adaptation. In particular, the criterion in this case takes account of the availability of the data and/or the measurement accuracy of the data and/or the amount of data and/or the type of data and/or the type or amount of different modalities of the data and/or characteristic features of the object region in the form of the type or characteristic of the tissue or material in the object region and/or characteristic features of the item in the form of its dimensions or material properties and/or characteristic features of devices of the arrangement in the form of settings or properties of individual components or the illumination setting and/or properties of the method in the form of its suitability for the present data or its speed or accuracy or the quality of the currently calculated 3-D reconstruction and/or the quality of the currently calculated relative position of the section of the item. These measures lead to a greater accuracy of the 3-D reconstruction of the object region volume and/or of the item and/or to a greater accuracy of the relative position of the section of the item in the 3-D reconstruction of the object region volume. This facilitates more comprehensive automation of the method.

Below, advantageous exemplary embodiments of the invention are described on the basis of the schematic drawings,
in which.

FIG. 5A, and

Figure 5A:
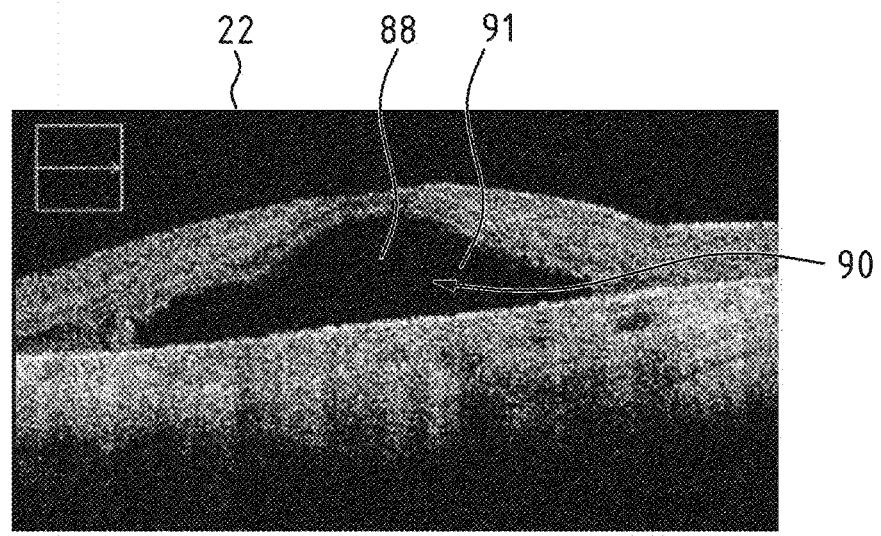
Figure 5B:
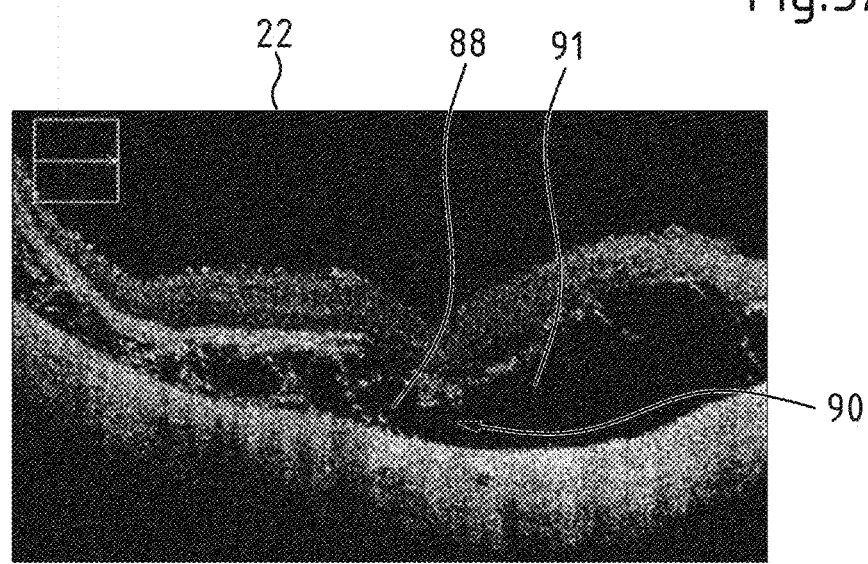
Figure 6:
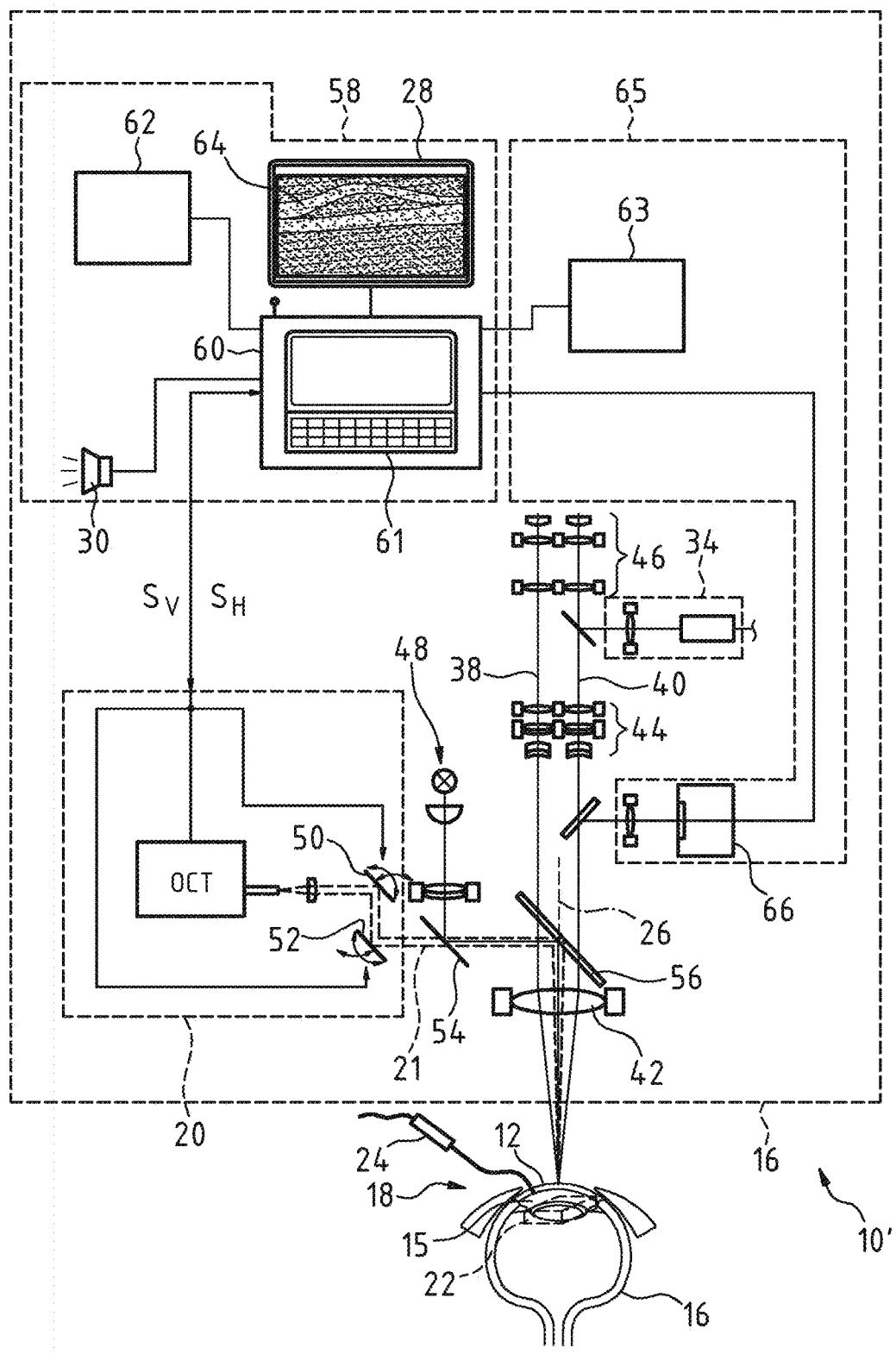
Figure 7:
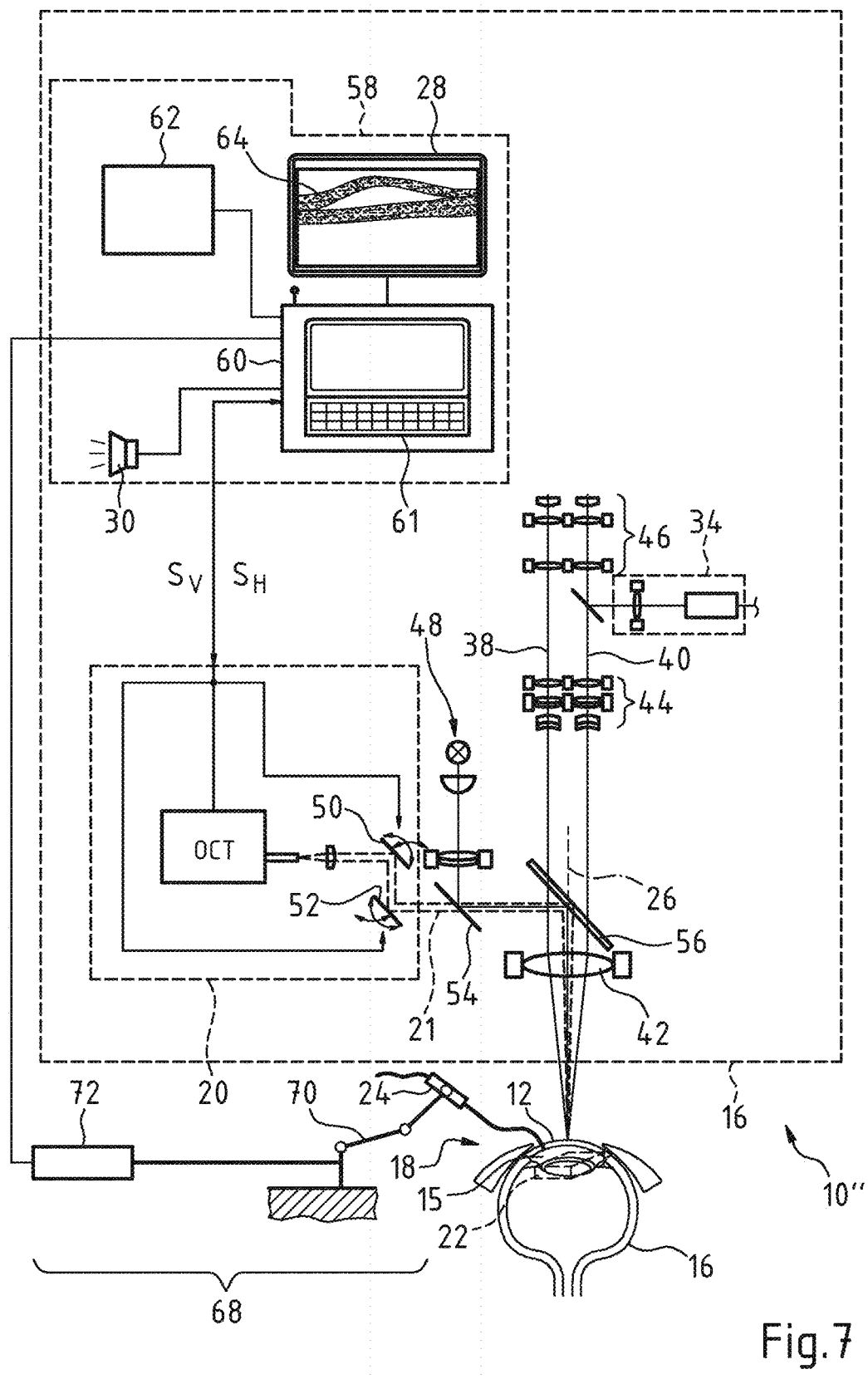
Figure 8:
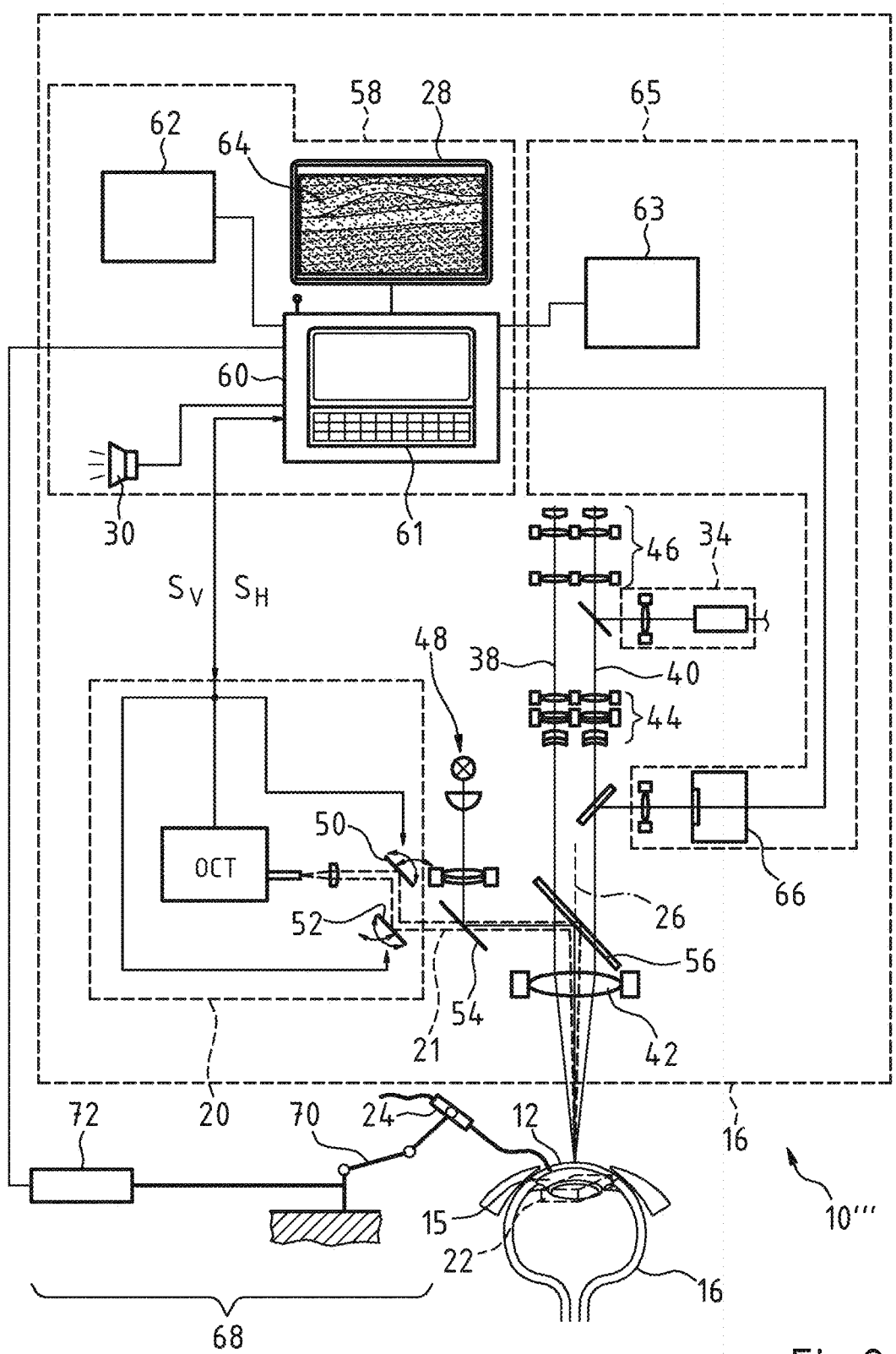
Figure 9:
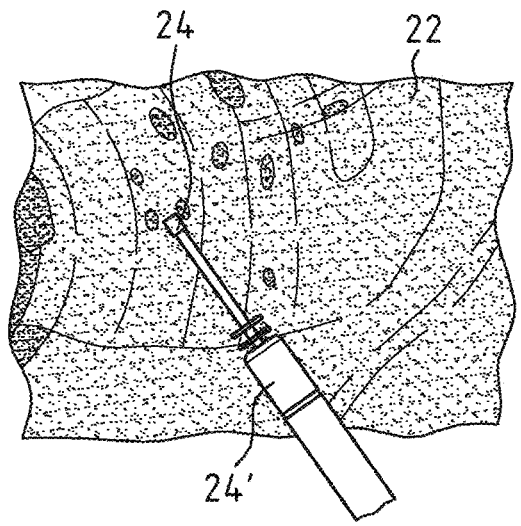
Figures 10A, 10B:
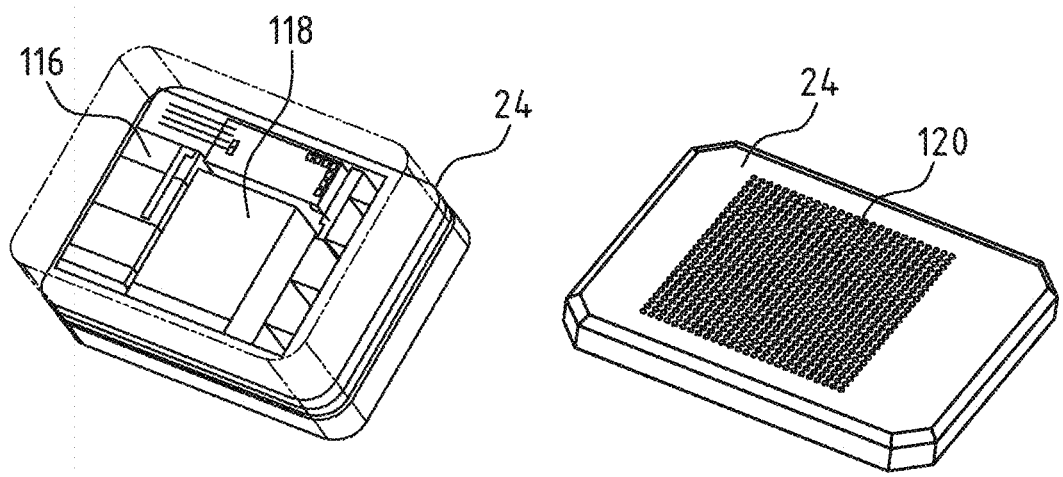
Figure 10C:
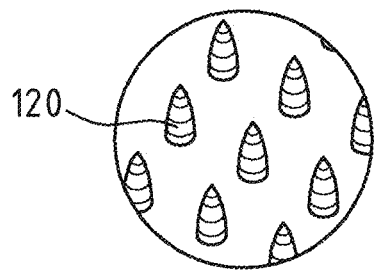
Figure 11:
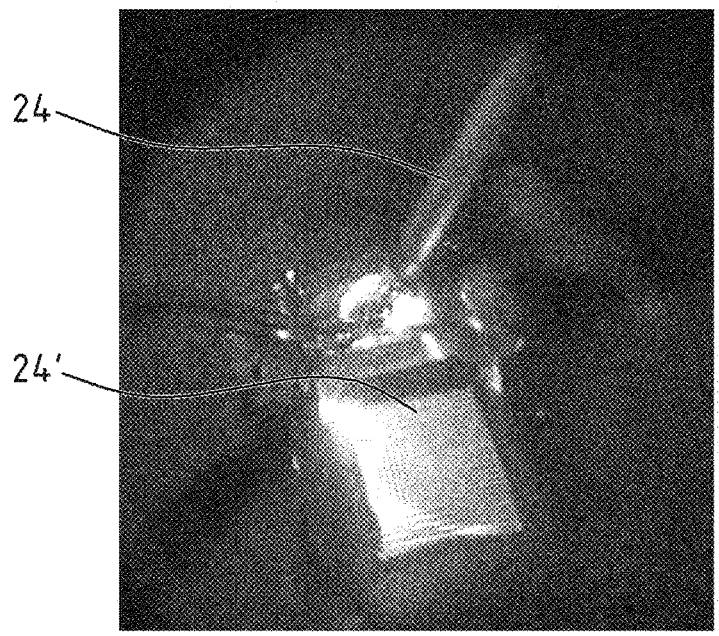
Figure 12:
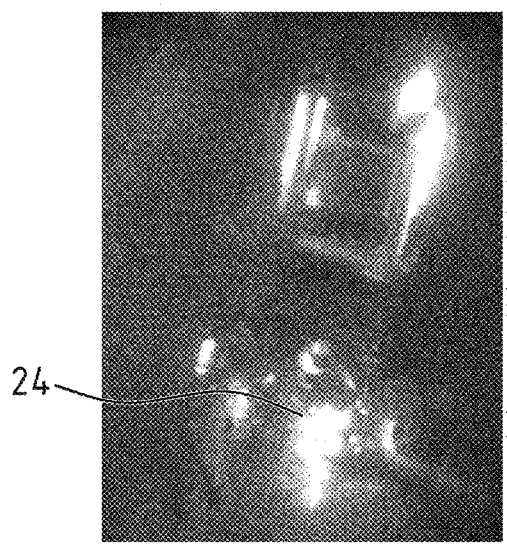
Figure 13:
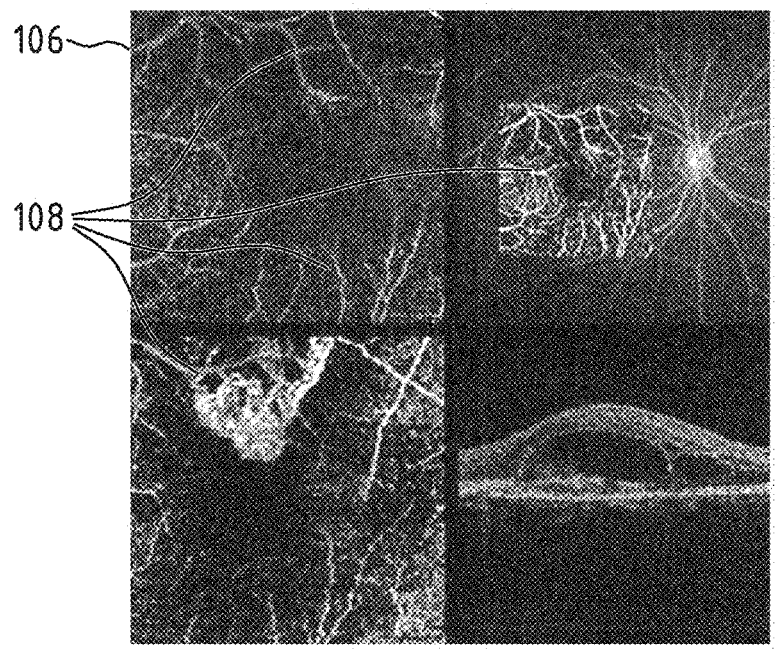
Figure 14:
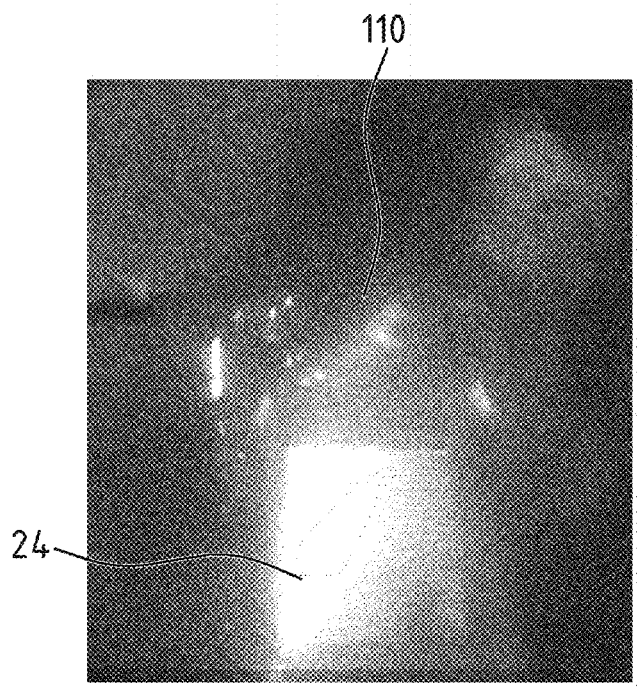
Figure 15:
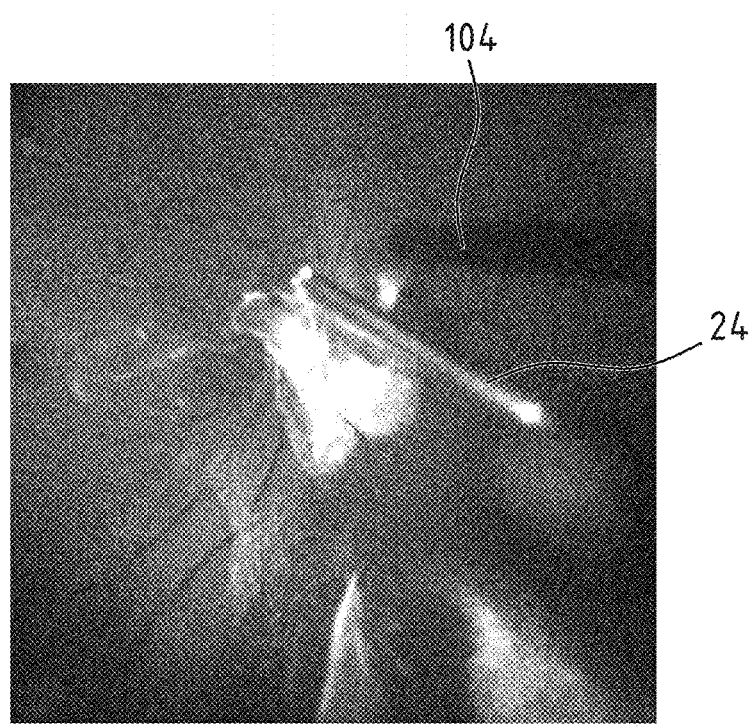

FIG. 5B show image data relating to OCT-B-scans of an object region volume with inhomogeneities during the stem cell injection;

FIG. 6 shows a second arrangement having a surgical microscope, having an OCT device for scanning an object region, having an item in the form of a surgical instrument and having an image providing device;

FIG. 7 shows a third arrangement having a surgical microscope, having an OCT device for scanning an object region, having an item in the form of a surgical instrument and having a robotic unit;

FIG. 8 shows a fourth arrangement having a surgical microscope, having an OCT device for scanning an object region, having an item in the form of a surgical instrument, having an image providing device and having a robotic unit;

FIG. 9 shows an item in the form of an applicator for a further item in the form of a retinal pin;

FIG. 10A shows a front side of an item in the form of an implant for the retina;

FIG. 10B shows a back side of an item in the form of an implant for the retina;

FIG. 10C shows a magnified partial view of an item in the form of an implant with 3-D electrodes;

FIG. 11 shows a first image of an operating region in the eye interior of a patient's eye captured by means of a camera, having an applicator for a retinal pin and having an implant;

FIG. 12 shows a further image of the operating region in the eye interior of a patient's eye captured by means of a camera, having the applicator for a retinal pin and having the implant;

FIG. 13 shows an image of an operating region in the eye interior of a patient's eye captured by means of a camera, having a vitrectome for vitrectomy that produces a shadowed region;

FIG. 14 shows images of the ocular fundus of a patient's eye based on OCT angiography data for the visualization of blood vessels; and FIG. 15 shows an image of an operating region in the eye interior of a patient's eye captured by means of a camera, having an implant and having blood flowing out of an injured blood vessel on the retina of the patient's eye.

Figure 1:
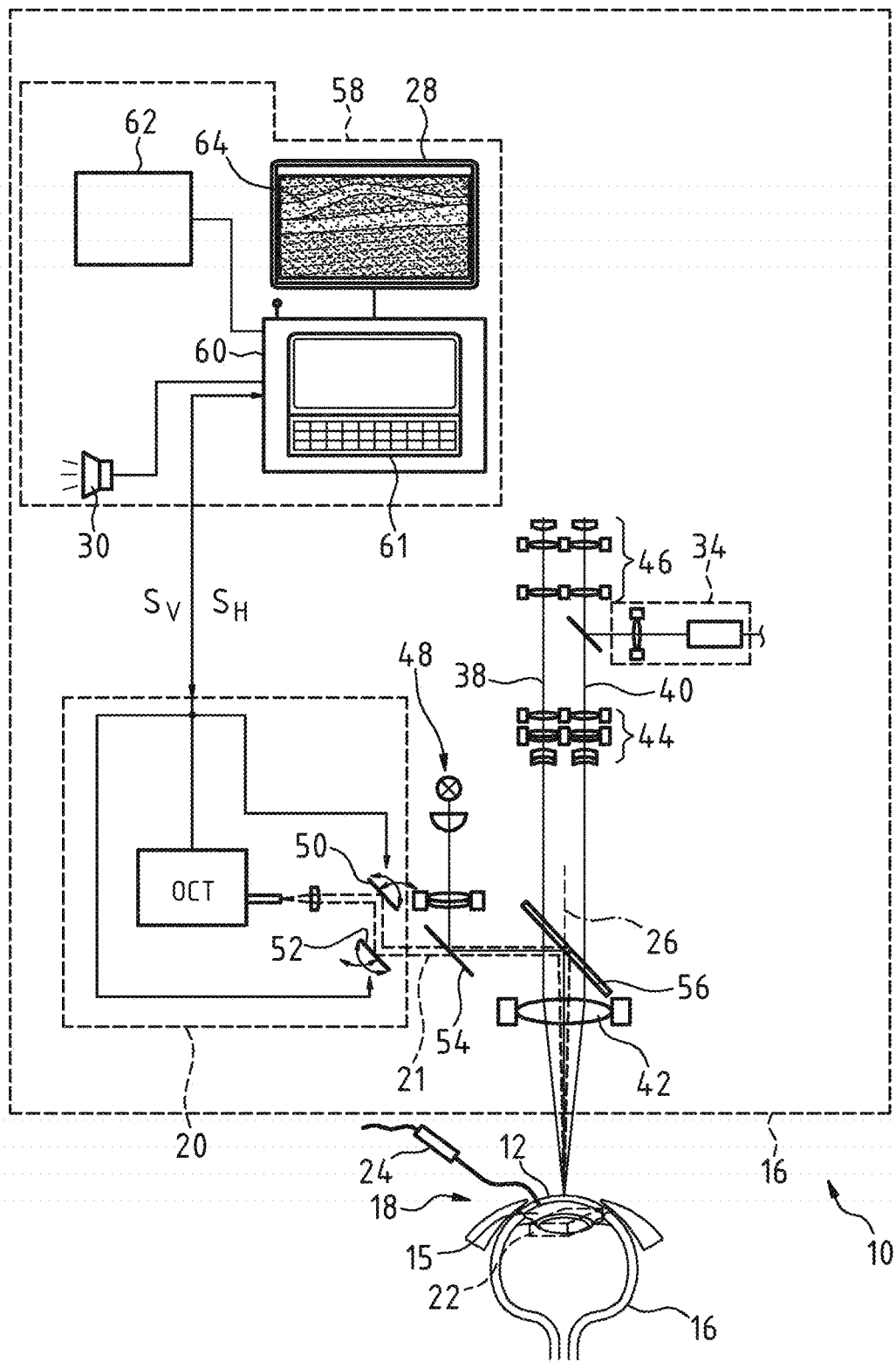
FIG. 1 shows a first arrangement having a surgical microscope, having an OCT device for scanning an object region and having an item in the form of a surgical instrument in the form of an injection needle therein.

The arrangement 10 shown in FIG. 1 contains a surgical microscope 16 for visualizing the object region 18 with magnification. By way of example, the surgical microscope 16 can be the OPMI® Lumera 660 Rescan surgical microscope by Carl Zeiss Meditec AG. The arrangement 10 comprises an OCT device 20 which provides an OCT scanning beam 21 for scanning the object region volume 22 with an A-, B- and C-scan at the patient's eye 14, as described, e.g., in chapter 3, pages 45 to 82 in A. Ehnes, "Entwicklung eines Schichtsegmentierungsalgorithmus zur automatischen Analyse von individuellen Netzhautschichten in optischen Koharenztomographie—B-Scans", Dissertation, University of Giessen (2013).

The arrangement 10 comprises an item 24 in the form of a surgical instrument which has a section 84 that is arrangeable in the object region 18 and localizable in the object region volume 22 by means of the OCT device 20 on the basis of a marker 78.

The surgical microscope 16 comprises a stereoscopic observation beam path 38, 40, which facilitates the examination of the patient's eye 14 through a microscope main objective 42 in the object region 18. The surgical microscope 16 further comprises a zoom system 44 and an eyepiece 46. It comprises an illumination device 48 which illuminates the object region 18 with illumination light through the microscope main objective 42 for the purposes of stereoscopically visualizing the patient's eye 14 in the eyepiece 46.

The OCT device 20 provides the OCT scanning beam 21 with short coherent light, which is guided through the microscope main objective 42 to the object region 18 in an object region volume 22 by way of adjustable scanning mirrors 50, 52 and beam splitters 54 and 56. The light of the OCT scanning beam 21 scattered in the object region volume 22 returns at least in part to the OCT device 20 via the same light path. Then, the light path of the scanning light is compared in the OCT device 20 to a reference path. Using this, it is possible to detect the precise position of scattering centers in the object region 18, in particular the position of optically effective areas, with an accuracy which corresponds to the coherence length $I_c$ of the short coherent light in the OCT scanning beam 21.

In the surgical microscope 16, there is a device 58 for controlling the OCT scanning beam 21 and for setting the position of the object region volume 22 scanned by the OCT scanning beam 21 in the object region 18. The device 58 contains a computer unit 60. The computer unit 60 has an input interface 61 as a means for entering target values and contains a computer program for controlling the OCT scanning beam 21 and adjusting the spatial extent and position, i.e., the relative position and orientation, of the object region volume 22 scanned by the OCT scanning beam 21. The device 58 for controlling the OCT scanning beam 21 is embodied in this case for successive continuous scanning of the object region volume 22 and of the region of the object region volume 22 containing the section 84 of the item 24 by means of the OCT scanning beam 21. In this case, the OCT scanning beam 21 has a frame rate of 10 ms to 20 ms in order to allow the surgeon to have fast hand-eye coordination.

The device 58 for controlling the OCT scanning beam 21 contains a display unit 28, connected to the computing unit 60, in the form of a display for displaying a user interface, on which the object region volume 22 with the section 84 of the item 24, scanned on the patient's eye 14 by means of the OCT scanning beam 21 is able to be visualized on the basis of an image 64. Moreover, in the arrangement 10, the OCT scanning information for the OCT device 20 may be visualized for a surgeon in the eyepiece 46 of the surgical microscope 16 by means of a device for overlaying data 34.

The computer unit 60 connected to the OCT device 20 additionally generates indication signals by means of a signal generator 30. In the case of the stem cell injection, an indication signal produced as an acoustic signal is generated by means of the signal generator 30 when the injection location is reached. Moreover, a variable in the form of the amount of stem cells still to be injected, which is derived from the guide variable, is a generated on the basis of a visual indication signal.

Further, the computer program in the program memory of the computing unit 60 contains a control routine which specifies the reference length for the OCT scanning beam 21 and the settings of the adjustable scanning mirrors 50, 52 for scanning the object region volume 22 in the object region with the patient's eye 14. There is a control member 62 in the form of an operating unit, actuatable by an operator, in the device 58 for setting the object region volume 22 scanned by means of the OCT scanning beam 21. The control routine moreover contains a scanning routine for scanning the object region volume 22 and the section 84 of the item 24 using specific scanning patterns. In the process, the object region volume 22 is scanned at a lower rate than the section 84 of the item 24 in order to keep the amounts of data as small as possible and hence the computation time as short as possible.

The computer program in the program memory of the computer unit 60 moreover serves to determine a 3-D reconstruction 94 of the object region volume 22 and the relative position of the section 84 of the item 24 in the object region volume 22 by processing scanning information obtained by the OCT device 20 by scanning the object region volume 22. In this case, the OCT scanning information, the 3-D reconstruction 94 and the relative position of the section 84 of the item 24 in the object region volume 22 are determined in real time. Moreover, the computer program contains a calculation routine for determining a target area 90 in the 3-D reconstruction 94 of the object region volume 22. A guide variable for the item 24 is determined in relation to the target area 90. Here, in the present case, a guide variable is understood to be a variable which is determined by the computer program and which serves to guide the item 24 in the object region 18.

Shadowing of regions in the object region volume 22 is avoided by virtue of the computer program containing a path planning routine which, on the basis of a criterion, calculates an optimal path of the item 24 to the spatial target position 91 in the target area 90 of the object region volume 22. In this case, the path planning routine determines a measure of shadowing in the form of a value which quantifies the presence of the shadows in the OCT data.

If the light source position is known, the region shadowed by the item 24 in the OCT data is calculated in advance for a certain path of the item 24 on the basis of the calculated relative position of the item 24. The measure of shadowing in this case denotes the magnitude of shadowing. On the basis of the measure of shadowing, the path planning routine then determines the shortest path of the item 24 to the target position 91 which does not exceed a threshold of the measure of shadowing. Alternatively, the path planning routine minimizes a criterion of the summation of the path length and the weighted measure of shadowing in order to determine a path which minimizes both the path length and the measure of shadowing to the greatest possible extent. The computer program contains a visualization routine for visualizing the optimal path of the item 24 for the surgeon using the display unit 28. In this case, planning the path for an item 24 to a target area 90 represents a guide variable.

It should be observed that the computer program may contain a shadowing routine for the prevention of shadowing of regions in the object region volume 22, said shadowing routine identifying the regions shadowed by the item 24 and specifying a compensation rule for the 3-D reconstruction 94 of the object region volume 22 in relation to these regions. In this case, the compensation rule provides for the replacement of the shadowed regions.

OCT data of the same regions at other recording times, in particular OCT data just preceding the shadowing of the shadowed region, can be used both for identifying and for replacing the shadowed regions in the 3-D reconstruction 94.

When injecting stem cells into the retina 15, a target value for the volume of the amount of a medium 88 in the form of stem cells that should be released by the injection needle is determined as a guide variable.

Figure 2:
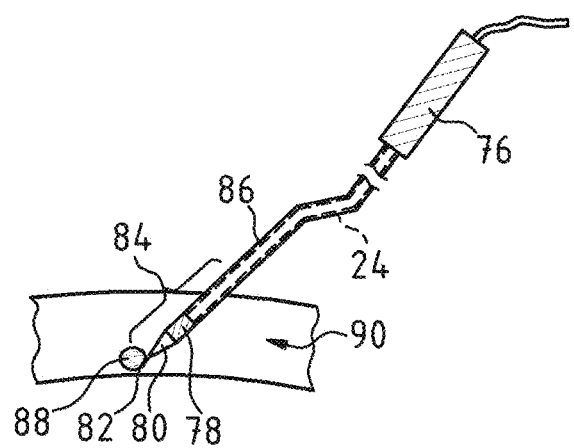
FIG. 2 shows a magnified view of the surgical instrument.

FIG. 2 is a magnified view of the item 24 in the form of a surgical instrument.

The surgical instrument is an injection needle for injecting stem cells in the retina 15 of the patient's eye 14. The injection needle has a section 84 which acts as an effective section and has a handle section 76 which can be held by a surgeon or, as an alternative thereto, by a micro-robot 70, too. The injection needle contains a capillary 86 and has a tip 80 with an opening 82 for releasing a medium 88 in the target area 90. There is a marker 78 that is localizable by means of the OCT scanning beam 21 at the injection needle.

It should be observed that the surgical instrument may also be in the form of an applicator for a retinal pin for placing an implant on the retina 15 of the patient's eye 14 or as a vitrectome for removing the vitreous humor from the patient's eye 14. It should moreover be observed that, in principle, the arrangement 10 can also be used for surgery on other body parts to a patient's eye 14.

Figure 3:
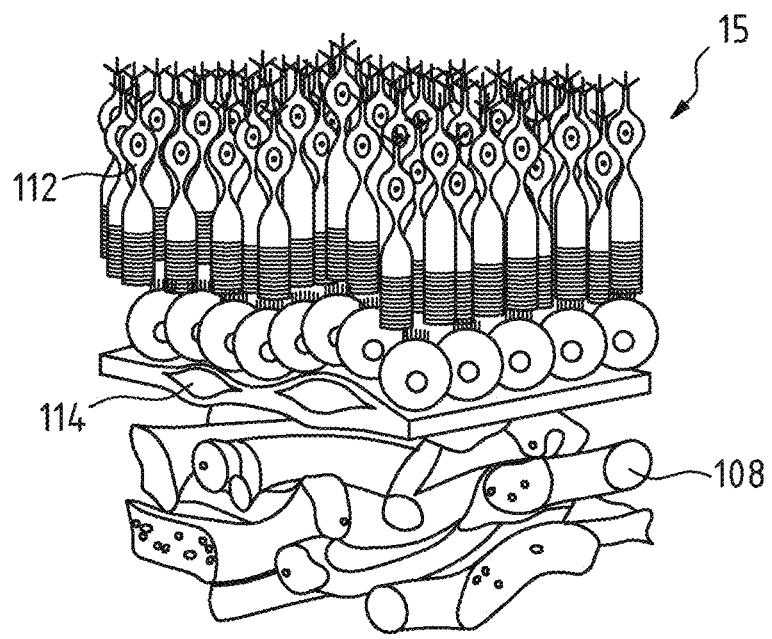
FIG. 3 shows a section of a portion of the retina.

FIG. 3 shows the structure of the retina 15 of the patient's eye 14, comprising blood vessels 108 as well as photoreceptors 112 and drusen 114.

Figure 4:
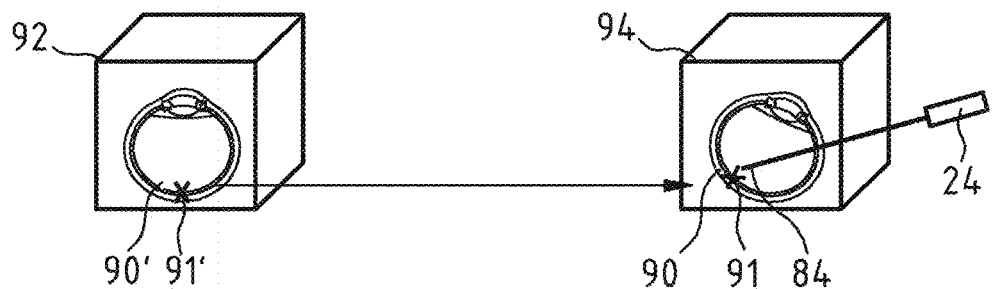
FIG. 4 shows a transfer of a target area based on data determined presurgery to a 3-D reconstruction of an object region volume.

FIG. 4 shows a transfer of a target area 90' based on data 92 determined presurgery to a 3-D reconstruction 94 of an object region volume 22 in the computer unit 60. To determine a target area 90 and a target position 91 in the 3-D reconstruction 94 of the object region volume 22, data 92 of the object region 18 determined presurgery are combined by calculation in said 3-D reconstruction with a target position 91' in a target area 90'. Here, the target position 91' denotes a location in the data 92 determined presurgery that relate to the object region volume 22, at which the item 24 should carry out a certain function. When injecting stem cells, the intended position 91' in the target area 90' in the data 92 determined presurgery corresponds to the envisaged location for the stem cell injection in the retina 15.

Methods for segmenting the tissue structures and tissue layers are applied for the purposes of determining the target position 91' and/or the target area 90' in the data 92 determined presurgery. Alternatively, the target position 91' and/or the target area 90' can also be marked by a surgeon in the data 92 determined presurgery.

The target position 91' and/or the target area 90' are transferred by the computer program from the data 92 of the object region volume 22 determined presurgery to the 3-D reconstruction 94 of the object region volume 22 determined from scanning information obtained by scanning the object region volume 22 and optionally from further data. In this case, a registration method serves for the transfer, said registration method mapping the target position 91' in the target area 90' in the data 92 determined presurgery to the target position 91 in the target area 90 of the object region volume 22. Alternatively, the surgeon can also directly mark the target position 91 and/or the target area 90 in the 3-D reconstruction 94 of the object region volume 22.

Then, the guide variable is determined by processing data of the target area 90' in the data 92 determined presurgery or of the 3-D reconstruction 94 of the object region volume 22. When injecting stem cells, a guide variable is determined in the form of the amount of stem cells still to be released.

In this respect, FIG. 5A and FIG. 5B each show an OCT-B-scan of the object region volume 22 with stem cells released at a target position 91 in a target area 90, with the OCT-B-scans having injection inhomogeneities.

To monitor and control the amount of stem cells injected, an actual value of the volume of the amount of stems cells released at the target position 91 in the target area 90 of the object region volume 22 is determined by comparing OCT scanning information of the target area 90 obtained by the OCT device 20 by scanning the object region volume 22 from before and during the release of the stem cells. In this case, the amount of stem cells injected is determined by means of image processing. To determine the volume change, it is possible for example to evaluate difference images which emerge as the difference of OCT scanning information items acquired at different times and/or the difference of 3-D reconstructions 94 determined at different times. Should the injected amount of stem cells contain particles visible to the OCT scanning radiation, the difference images could also be used to determine, by way of image processing, the location of leakages in the object region volume 22. Leakages possibly present are taken into account by these measures and it is ensured that the specified amount of stem cells are in fact injected at the injection location. If necessary, the injection location, that is to say the target position of the injection needle, may also be adjusted during the stem cell injection.

On the basis of a target value for the amount of stem cells to be injected, specified by the surgeon, the guide variable in the form of the amount of stem cells still to be released is determined from the difference between target value and determined actual value of the amount of stem cells released. For readjusting the amount of stem cells, the computer program generates indication signals for a surgeon and/or control signals for the injection needle, which are transmitted to the control unit 72 of a micro-robot 70 guiding the injection needle, until the specified amount of stem cells are obtained at the target position 91 in the target area 90.

In this case, an indication signal is generated for the surgeon by the signal generator 30, said indication signal specifying the amount of stem cells still to be released or the amount of stem cells already released. The indication signal is represented in the form of a bar on the display of the display unit 28. On the basis of the signal, the surgeon can carry out the injection of stem cells themselves or monitor the injection procedure by the micro-robot 70.

FIG. 6 shows a second arrangement 10' having a surgical microscope 16, having an OCT device 20 for scanning an object region 18, having an item 24 in the form of a surgical instrument and having an image providing device 65. To the extent the components and elements of the second arrangement 10' shown in FIG. 6 correspond to the components and elements of the first arrangement 10 visible in FIG. 1, these have been identified with the same numbers as reference signs.

The image providing device 65 contains an image capturing device 66, by means of which images of the patient's eye 14 can be captured in real time. In addition or as an alternative thereto, the image providing device 65 contains a memory 63, in which data 92 determined presurgery that relate to the object region are provided. The images of the patient's eye 14 and the data 92 determined presurgery are used in addition to the data obtained by scanning the object region volume 22 by means of the OCT scanning beam 21 of the OCT device 20 in order to calculate the 3-D reconstruction 94 so as to obtain greater accuracy in the process. It should be observed that, in principle, biometric patient data may also be used when creating the 3-D reconstruction 94 of the object region volume 22, for example an eye length, an eye diameter, white-to-white, a corneal thickness, an anterior chamber depth or anterior chamber angle.

A registration method is used for determining the relative spatial position of different data in relation to one another and for combining different data sources, said registration method processing scanning information obtained by the OCT device 20 by scanning the object region volume 22 and data 92 determined presurgery, target positions 91 for the items 24, 24' and, if present, further data of the object region volume 22. This permits simultaneous use of all acquired data in every visualization of the object region volume 22.

FIG. 7 shows a third arrangement 10" having a surgical microscope 16, having an OCT device 20 for scanning an object region 18, having an item 24 in the form of a surgical instrument and having a robotics unit 68. To the extent the components and elements of the third arrangement 10" shown in FIG. 8 correspond to the components and elements of the first arrangement 10 visible in FIG. 1 or the components and elements of the second arrangement 10' visible in FIG. 6, these have been identified with the same numbers as reference signs.

The robotics unit 68 comprises a micro-robot 70 with a control unit 72. By way of example, the micro-robot 70 can be in the form of a manipulator for surgical instruments with motor drives, as provided in the ophthalmic surgical operating system R1.1 by Preceyes B. V.

To ensure automation of the operation that is as comprehensive as possible, a movement of the item 24 embodied as a surgical instrument in the form of an injection needle is set in this case by means of the micro-robot 70. The micro-robot 70 of the robotics unit 68 is controlled in this case on the basis of the information items processed by the computer unit 60.

The control signals generated by the computer unit 60 for adjusting the micro-robot 70 in the robotics unit 68 are guide variables for the item 24, which is embodied as a surgical instrument in the form of an injection needle, in the third arrangement 10'''.

It should be observed that, in place of an item 24 embodied as a surgical instrument in the form of an injection needle, the micro-robot can in principle also move an item in the form of a surgical instrument embodied as an applicator or as a retinal pin or as a vitrectome in order to guide the item to a target area 90 in the object region volume 22. Offset information, which specifies the spatial offset of the section 84 of the item 24 from the spatial target position 91, can also be calculated to this end by the computer program on the basis of the target area 90 determined in the object region volume 22 and the determined relative position of the item 24. Then, control signals for displacing the item 24 are generated from the offset information and are transmitted to the control unit 72 of the micro-robot 70.

FIG. 8 shows a fourth arrangement 10"' having a surgical microscope 16, having an OCT device 20 for scanning an object region 18, having an item 24 in the form of a surgical instrument and having a robotics unit 68, and having an image providing device 65. To the extent the components and elements of the fourth arrangement 10''' shown in FIG. 9 correspond to the components and elements of the arrangements 10, 10', 10" which are visible in FIG. 1, FIG. 6 and FIG. 7 and described on the basis of these figures, these have been identified with the same numbers as reference signs. The image providing device 65 with the image capturing device 66 in this case facilitates, in turn, a calculation of the 3-D reconstruction 94 of a patient's eye 14 with an accuracy that is greater than a 3-D reconstruction which is based exclusively on scanning information obtained by means of an OCT device 20.

It should be observed that, during the vitrectomy by means of a surgical instrument also in the form of a vitrectome, the amount of vitreous humor to be removed from the respective point of the retina 15 may also be specified as a guide variable in the arrangements described above.

It should moreover be observed that if the surgical instrument is also in the form of a vitrectome, an amount of vitreous humor to be removed from the patient's eye 14 can also be indicated as a display signal in the arrangements 10, 10', 10", 10''' described above.

FIG. 9 shows an item 24 embodied as a surgical instrument in the form of an applicator for placing a further item 24' in the form of a retinal pin, which serves to fasten a further item in the form of an implant to the retina 15.

FIG. 10A and FIG. 10B show an implant for the retina 15 of a patient's eye 14 as an item 24, said implant containing a power source 116 with a photovoltaic assembly and an image capture assembly 118. In this case, FIG. 10A is a perspective view of the implant in the case of a viewing direction directed at the side facing away from the retina. FIG. 10B is a perspective view of the implant in the case of a viewing direction on a side facing the retina of the patient's eye 14. FIG. 10C is a magnified partial view of the implant. The implant has 3-D electrodes 120, which penetrate into the retina 15 and interact with the neural network of the nerve tracts there.

In the apparatuses 10, 10', 10", 10''' described above, the target position 91 of the envisaged location of attachment of the retinal pin to the retina 15 of the patient's eye and the actual position of the item 24, in the form of an implant, on the retina 15 can be displayed on the display unit 28 for the purposes of attaching an implant in a patient's eye 14.

FIG. 11 shows a first image of an operating region in the eye interior of a patient's eye 14 captured by means of a camera, said image containing a first item 24 in the form of an applicator for a retinal pin and containing a further item 24' in the form of an implant just before the placement thereof on the retina 15. FIG. 12 shows a corresponding image of the operating region with the implant following the placement thereof on the retina 15. After the implant has been attached to the retina, the seat of the implant is verified by virtue of, e.g., the surgeon examining whether the implant fulfils its intended physiological function. When an implant is attached to the retina 15 of a patient's eye 14, a guide variable in the form of a control signal for the displacement of an applicator for attaching a retinal pin for fastening the implant is generated by the computer program and transmitted to the surgeon or the control unit 72 of the micro-robot 70.

FIG. 13 shows images 106 of the ocular fundus of a patient's eye 14 based on OCT angiography data for the visualization of blood vessels. In the above-described arrangements 10, 10', 10", 10''', corresponding OCT angiography data can be generated from the scanning information obtained by the OCT device 20 by scanning the object region volume 22 and can be displayed on the display unit 28. The images 106 show the course of the blood vessels 108 in the object region 18. The position and/or the dimensions such as the diameter or the length of the blood vessels 108 is determined by the computer program on the basis of the images 106 that are based on OCT angiography data, for example by means of image processing. This information then is taken into account when determining the target positions 91 of the items 24, 24' in the target area 90 in the 3-D reconstruction 94 of the object region volume 22. In particular, the number of blood vessels 108 to be punctured is minimized when determining the spatial target position 91 for an item 24, 24' in the target area 90.

FIG. 14 shows an image of an operating region in the eye interior of a patient's eye 14 captured by means of a camera, having an implant and having blood flowing out of an injured blood vessel 108 on the retina 15 of the patient's eye 14.

OCT angiography data from the scanning information obtained by the OCT device 20 by scanning an object region volume 22 allow the prevention of hemorrhaging 110 as a result of injuring relatively large blood vessels 108 in the case of ophthalmic-surgical operations.

FIG. 15 is an image, captured by means of a camera, of an operating region in the eye interior of a patient's eye 14, in which an item 24 in the form of a vitrectome for vitrectomy is positioned, as a result of which a region 104 of the patient's eye 14 is shadowed. An exact vitrectomy without remains is important for the success of retinal implant surgery, as it facilitates an improved signal-to-noise ratio.

Hence, for the vitrectomy within the scope of an ophthalmic surgical operation by means of a vitrectome, the target position 91 of the latter in the target area 90 can be displayed on the display unit 28 in the above-described apparatuses 10, 10', 10", 10''' as the location in the 3-D reconstruction 94 of an object region volume 22 where the vitreous humor should be removed.

Hence, the computing routine of the computer programs in the computer unit 60 of the above-described arrangements 10, 10', 10", 10''' is designed for the vitrectomy by means of a vitrectome, in such a way that an amount of vitreous humor to be removed is determined as a guide variable by processing the target area 90 in the 3-D reconstruction 94 of the object region volume 22. Alternatively, the amount of vitreous humor to be removed can also be determined by processing data 92 determined presurgery or by the input of a target value by a surgeon. In this case, the vitreous humor is identified by injecting the triamcinolone marker, as is evident from FIG. 15, in order to facilitate a more accurate identification of the vitreous humor and hence a removal thereof without remainder where possible. In this case, the vitreous humor to be removed is visualized to the surgeon on the basis of a contour map which indicates for each point on the retina 15 the amount of the vitreous humor, located thereabove, to be removed. Moreover, during the vitrectomy, the computer program continuously indicates to the surgeon a boundary between the vitreous humor and a solution (BSS) for rinsing the object region 18. As a result, the amount of vitreous humor to be removed can be determined automatically by means of image processing and can be displayed in the visualization of the operating region by way of the display unit.

Further guide variables in the form of control signals for displacing the surgical instrument in the form of the injection needle or the vitrectome are generated both when injecting stem cells and when removing vitreous humor, and said further guide variables are transmitted to the surgeon or to the control unit 72 of the micro-robot 70.

FIG. 15 moreover shows a region 104 in an object region volume 22 that is shadowed by an item 24 in the form of a vitrectome. The computer program contains a shadowing routine to prevent the shadowing of regions in the object region volume 22. It identifies regions 104 shadowed by the item 24 and specifies a compensation rule for the 3-D reconstruction 94 of the object region volume 22 for these regions. In this case, the compensation rule provides for the replacement of the shadowed regions. OCT data of the same regions at other recording times, in particular OCT data just preceding the shadowing of the shadowed region 104, can be used both for identifying and for replacing the shadowed regions 104 in a 3-D reconstruction 94 shown in FIG. 15. As an alternative thereto, the shadowing routine for recognizing shadowed regions and/or for specifying the compensation rule may use the current 3-D reconstruction 94 and/or the currently recorded OCT data and/or data from other modalities relating to the same region, for example optical data, MRI data, ultrasound images or CT data. Data 92 determined presurgery may also be used. Alternatively, the shadowed regions 104 may also be detected in the 3-D reconstruction 94 and may be replaced by data acquired from other regions outside of shadowed regions 104. Alternatively, the shadowed regions 104 may be detected in the data or in the 3-D reconstruction 94 and may be replaced by data generated by the computer program, for example by way of inpainting methods.

Shadowing of regions can be avoided by virtue of the computer program containing a path planning routine which, on the basis of a criterion, calculates an optimal path of the item 24 to the spatial target position 91 in the target area 90 of the object region volume 22. In this case, the path planning routine determines a measure of shadowing in the form of a value which quantifies the presence of the shadows in the OCT data. If the light source position is known, the region 104 shadowed by the item 24 in the OCT data is calculated in advance for a certain path of the item 24 on the basis of the calculated relative position of the item 24. The measure of shadowing in this case denotes the magnitude of shadowing. On the basis of the measure of shadowing, a path planning routine then determines the shortest path of the item 24 to the target position 91 which does not exceed a threshold of the measure of shadowing. Alternatively, the path planning routine minimizes a criterion of the summation of the path length and the weighted measure of shadowing in order to determine a path which minimizes both the path length and the measure of shadowing to the greatest possible extent. The computer program contains a visualization routine for visualizing the optimal path of the item 24 for the surgeon using the display unit 28. In this case, planning the path for an item 24 to a target area 90 represents a guide variable.

It should be observed that both the input data of the 3-D reconstruction method and the input data of the registration method are adjusted where possible during the operation to the availability and the measurement accuracy of the provided data in order to obtain a greater accuracy for the 3-D reconstruction 94 of the object region volume 22. If the measurement accuracy of individual data points is too low, these are not taken into account by the respective method.

In summary, the following, in particular, should be noted: The invention relates to an arrangement 10, 10', 10", 10''' comprising an OCT device 20 for scanning an object region volume 22, arranged in an object region 18, by means of an OCT scanning beam 21, comprising an item 24, which has a section 84 in the object region volume 22 that is arrangeable in the object region 18 and is localizable in said object region volume 22 by means of the OCT device 20, and comprising a computer unit 60 which is connected to the OCT device 20 and which contains a computer program for determining a 3-D reconstruction 94 of the object region volume 22 and determining the relative position of the section 84 of the item 24 in the object region volume 22 by processing OCT scanning information obtained by the OCT device 20 by scanning the object region volume 22, wherein the computer program has a computing routine for determining a target area 90 in the 3-D reconstruction 94 of the object region volume 22, said computing routine determining a guide variable for the item 24 in relation to the target area 90.

In particular, the invention relates to the following aspects specified in clauses:

1. An arrangement (10, 10', 10", 10''')
    comprising an OCT device (20) for scanning an object region volume (22) in an object region (18) by means of an OCT scanning beam (21);
    comprising an item (24, 24') which has a section (84) that is arrangeable in the object region volume (22) and is localizable there by means of the OCT device (20), and
    comprising a computer unit (60) which is connected to the OCT device (20) and which contains a computer program for determining a 3-D reconstruction (94) of the object region volume (22) and determining the relative position of the section (84) of the item (24, 24') in the object region volume (22) by processing OCT scanning information obtained by means of the OCT device (20) by scanning the object region volume (22),
    characterized in that
    the computer program has a computing routine for determining a target area (90) in the 3-D reconstruction (94) of the object region volume (22), said computing routine determining a guide variable for the item (24, 24') in relation to the target area (90).

2. The arrangement (10, 10', 10", 10''') according to clause 1, characterized
    in that the computer program is designed to determine a 3-D reconstruction (94) of the object region volume (22) from data which are obtained by examining the object region volume (22) using an imaging method, in particular by scanning the object region volume (22) by means of the OCT scanning beam (21) of the OCT device (20), and/or which are data (92) determined presurgery and/or which are data relating to sensor signals for determining a position of the section (84) of the item (24, 24') in the object region volume (22);
    and/or
    in that the computer program is designed to determine the relative spatial position of data in relation to one another by means of a registration method, said data comprising data from the following group: scanning information obtained by means of the OCT device (20) by scanning the object region volume (22), the object region volume (22), data from further imaging methods, in particular optical image representations, MRI data, CT data, ultrasound images, endoscopy images, a position of the section (84) of the item (24), data (92) determined presurgery, position sensor signals;
    and/or
    in that the OCT device (20) is designed for successive continuous scanning of the object region volume (22) by means of the OCT scanning beam (21) and/or in that the OCT device (20) is designed for successive continuous scanning of a region of the object region volume (22) containing the section (84) of the item (24, 24') by means of the OCT scanning beam (21);
and/or
in that the computer program is designed for successive continuous determination of the 3-D reconstruction (94) of the object region volume (22) and/or for successive continuous determination of the relative position of the section (84) of the item (24, 24') in the object region volume (22);
in that the computer program is designed to determine a spatial target position (91) for the item (24, 24') in the 3-D reconstruction (94) of the object region volume (22);
and/or
in that the computer unit (60) is connected to a memory (63) for the provision during surgery of the data (92) determined presurgery;
and/or
in that the computer program is designed to determine target areas (90') and/or spatial target positions (91') in data (92) determined presurgery and/or target areas (90) and/or spatial target positions (91) in the 3-D reconstruction (94) of the object region volume (22) by virtue of the application of methods for segmenting tissue structures and/or tissue layers;
and/or
in that the computer program contains a routine for generating a guide variable in the form of control signals for the item (24, 24');
and/or
in that the computer program is designed to determine as a guide variable a spatial target position (91) in the target area (90) in the 3-D reconstruction (94) of the object region volume (22) taking account of characteristic features of the item (24) and/or of a further item (24') and/or of the target area (90) in the 3-D reconstruction (94) of the object region volume (22), and/or taking account of geometric relationships, in particular offset information, between these;
and/or
in that the arrangement comprises a device for visualizing the relative position of the section (84) of the item (24) in the 3-D reconstruction (94) of the object region volume (22) and/or for visualizing data (92) determined presurgery and/or for visualizing the guide variable determined in relation to the target area (90) and/or for visualizing variables derived from the guide variable;
and/or
in that the computer program generates acoustic, optical or haptic indication signals for the surgeon on the basis of the guide variable determined in relation to the target area (90) and/or variables derived therefrom;
and/or
in that that the computer program contains a shadowing routine for determining a corrected 3-D reconstruction (94) of the object region volume (22), said shadowing routine recognizing regions (104) that are shadowed by the item (24, 24') and specifying a compensation rule for the 3-D reconstruction (94) of the object region volume (22) in relation to these regions;
and/or
in that a marker (78) that is localizable by the OCT scanning beam (21) is arranged in the section (84) of the item (24, 24') and/or in the object region (18);
and/or
in that the computer program contains a scanning routine for scanning the object region volume (22) and/or the section (84) of the item (24, 24') using specific scanning patterns and/or for adjusting a scanning rate, which scans the object region volume (22) at a lower rate in comparison with the position of the section (84) of the item (24, 24');
and/or
in that the computer program is designed for adjusting the determination rule for the 3-D reconstruction (94) and/or the determination rule for the relative position of the section (84) of the item (24, 24') in the object region volume (22) on the basis of a criterion.

3. The arrangement (10, 10', 10", 10''') according to clause 1 or 2, characterized in that OCT angiography data (106) of the object region volume (22) are generated from the scanning information obtained by means of the OCT device (20) by scanning the object region volume (22).

4. The arrangement (10, 10', 10", 10''') according to clause 3, characterized in that the computer program is designed to determine the position and/or dimensions of blood vessels (108) in the target area (90) on the basis of the OCT angiography data (106), the computing routine of the computer program for determining the target area (90) in the 3-D reconstruction (94) of the object region volume (22) taking account of the course and/or the position and/or the dimensions of the blood vessels (108) in the target area (90).

5. The arrangement (10, 10', 10", 10''') according to any one of clauses 1 to 4, characterized in that the computer program contains a path planning routine which, on the basis of a criterion, calculates an optimal path of the item (24, 24') to the spatial target position (91).

6. The arrangement (10, 10', 10", 10''') according to clause 5, characterized in that the criterion is a measure of shadowing that quantifies the presence of shadows caused by the item (24, 24') in the calculated 3-D reconstruction (94).

7. The arrangement (10, 10', 10", 10''') according to any one of clauses 1 to 6, characterized in that the computer program contains a routine for determining a target area (90') and/or a target position (91') for the item (24) in provided data (92) determined presurgery and has a registration routine for registering the data (92) determined presurgery with the 3-D reconstruction (94) of the object region volume (22) and a transfer routine for transferring the target area (90') and/or the target position (91') in the data (92) determined presurgery to the 3-D reconstruction (94) of the object region volume (22).

8. The arrangement (10, 10', 10", 10''') according to any one of clauses 1 to 7, characterized in that the item (24, 24') is in the form of a surgical instrument which comprises a capillary (86) with an opening (82) for the release of a medium (88).

9. The arrangement (10, 10', 10", 10''') according to clause 8, characterized in that the computing routine of the computer program serves to determine as a guide variable a target value for the volume of the released medium (88) by processing the target area (90) in the 3-D reconstruction (94) of the object region volume (22) and/or by processing data (92) determined presurgery and/or by processing OCT scanning information obtained by means of the OCT device (20) by scanning the object region volume (22) and/or by way of an input of a target value by a surgeon.

10. The arrangement (10, 10', 10", 10''') according to clause 8 or 9, characterized in that the computing routine of the computer program serves to determine an actual value of the volume of the medium (88) released into the target area (90) by comparing data of the target area (90) in the 3-D reconstruction (94) of the object region volume (22) and/or scanning information of target area (90) obtained by means of the OCT device (20) by scanning the object region volume (22) before and during the release of the medium (88).
11. The arrangement according to any one of clauses 8 to 10, characterized in that the computing routine of the computer program is designed to determine as a guide variable for a readjustment of the volume of the released medium (88) a difference between a target value and an actual value of the volume of the medium (88) released into the target area (90).
12. The arrangement according to any one of clauses 1 to 7, characterized in that the computing routine of the computer program serves to determine as a guide variable the position of a substance to be removed and/or an amount of substance to be removed by processing the target area (90) in the 3-D reconstruction (94) of the object region volume (22) and/or by processing data (92) determined presurgery and/or by way of the input of a target value by a surgeon.
13. The arrangement (10, 10', 10", 10''') according to clause 12, characterized by a visualization routine for visualizing the position of the substance to be removed and/or an amount of substance to be removed in the object region volume (22).
14. A computer program for determining a 3-D reconstruction (94) of an object region volume (22) in an object region (18) and for determining the relative position of a section (84) of an item (24) in the object region volume (22) by processing OCT scanning information obtained by means of an OCT device (20) by scanning the object region volume (22), characterized by
determining a target area (90) in the 3-D reconstruction (94) of the object region volume (22) and a guide variable for the item (24) in relation to the target area (90).
15. A method for determining a 3-D reconstruction (94) of an object region volume (22) in an object region (18) and for determining the relative position of a section (84) of an item (24) in the object region volume (22) by means of a computer program according to clause 14.

LIST OF REFERENCE SKINS 10, 10', 10", 10''' Arrangement/apparatus
12 Cornea
14 Patient's eye
15 Retina
16 Surgical microscope
18 Object region
20 OCT device
21 OCT scanning beam
22 Object region volume
24, 24' Item
26 Optical axis
28 Display unit
30 Signal generator
34 Data overlay
38, 40 Stereoscopic observation beam path
42 Microscope main objective
44 Zoom system
46 Eyepiece
48 Illumination device
50, 52 Scanning mirror
54, 56 Beam splitter
58 Device
60 Computer unit
61 Input interface
62 Control member
63 Memory
64 Image
65 Image providing device
66 Image capturing device
68 Robotics unit
70 Micro-robot
72 Control unit
76 Handle section
78 Marker
80 Tip
82 Opening
84 Section
86 Capillary
88 Medium
90 Target area
90' Target area in data determined presurgery
91 Target position
91' Target position in data determined presurgery
92 Data determined presurgery
94 3-D reconstruction
104 Shadowed region
106 Images based on OCT angiography data
108 Blood vessel
110 Hemorrhaging
112 Photoreceptors
114 Druse
116 Power source
118 Image capture assembly
120 3-D electrodes

The invention claimed is:

1. An arrangement comprising:
an optical coherence tomography (OCT) device for scanning an object region volume in an object region by an OCT scanning beam;
an item which has a section that is arrangeable in the object region volume and is localizable there by the OCT device, and
a computer unit which is connected to the OCT device and which contains a computer program for determining a 3-D reconstruction of the object region volume and for determining a relative position of the section of the item in the object region volume by processing OCT scanning information obtained by the OCT device by scanning the object region volume,
wherein:
the computer program has a computing routine for determining a target area in the 3-D reconstruction of the object region volume,
the computing program containing a path planning routine that calculates an optimal path of the item to a spatial target position in the target area as a first guide variable to guide the item in the object region, the optimal path being calculated based on a first criterion, and
the first criterion being a measure of shadowing that quantifies a presence of shadows caused by the item in the calculated 3-D reconstruction.

2. The arrangement as claimed in claim 1, wherein the computer program is designed to determine the 3-D reconstruction of the object region volume from data which is obtained by examining the object region volume using an imaging method by scanning the object region volume by the OCT scanning beam of the OCT device, and/or which is data determined presurgery and/or which is data relating to sensor signals for determining the relative position of the section of the item in the object region volume.

3. The arrangement as claimed in claim 1, wherein the computer program is designed to determine relative spatial position of data in relation to one another by a registration method, said data comprising data from the following group: scanning information obtained by the OCT device by scanning the object region volume, data from further imaging methods of optical image representations, MRI data, CT data, ultrasound images, endoscopy images, the relative position of the section of the item, data determined presurgery, and/or position sensor signals.

4. The arrangement as claimed in claim 1,
wherein the OCT device is designed for successive continuous scanning of the object region volume by the OCT scanning beam; and/or
wherein the OCT device is designed for successive continuous scanning of a region of the object region volume containing the section of the item by the OCT scanning beam; and/or
wherein the computer program is designed for successive continuous determination of the 3-D reconstruction of the object region volume and/or for successive continuous determination of the relative position of the section of the item in the object region volume; and/or
wherein the computer program is designed to determine a spatial target position for the item in the 3-D reconstruction of the object region volume; and/or
wherein the computer unit is connected to a memory for the provision during surgery of data determined presurgery; and/or
wherein the computer program is designed to determine target areas and/or spatial target positions in the data determined presurgery and/or target areas and/or spatial target positions in the 3-D reconstruction of the object region volume by virtue of methods for segmenting tissue structures and/or tissue layers; and/or
wherein the computer program contains a routine for generating a second guide variable in a form of control signals for the item; and/or
wherein the computer program is designed to determine as a third guide variable a spatial target position in the target area in the 3-D reconstruction of the object region volume taking account of characteristic features of the item and/or of a further item and/or of the target area in the 3-D reconstruction of the object region volume, and/or taking account of geometric relationships between these; and/or
wherein the arrangement comprises a device for visualizing the relative position of the section of the item in the 3-D reconstruction of the object region volume and/or for visualizing the data determined presurgery and/or for visualizing the first guide variable determined in relation to the target area and/or for visualizing variables derived from the first guide variable; and/or
wherein the computer program generates acoustic, optical or haptic indication signals for a surgeon on the basis of the first guide variable determined in relation to the target area and/or variables derived therefrom; and/or
wherein the computer program contains a shadowing routine for determining a corrected 3-D reconstruction of the object region volume, said shadowing routine recognizing regions that are shadowed by the item and specifying a compensation rule for the 3-D reconstruction of the object region volume in relation to these regions; and/or
in that a marker that is localizable by the OCT scanning beam is arranged in the section of the item and/or in the object region; and/or
wherein the computer program contains a scanning routine for scanning the object region volume and/or the section of the item using specific scanning patterns and/or for adjusting a scanning rate, which scans the object region volume at a lower rate in comparison with the relative position of the section of the item; and/or
wherein the computer program is designed for adjusting a determination rule for the 3-D reconstruction and/or a determination rule for the relative position of the section of the item in the object region volume on the basis of a second criterion.

5. The arrangement as claimed in claim 1, wherein OCT angiography data of the object region volume is generated from the OCT scanning information obtained by the OCT device by scanning the object region volume.

6. The arrangement as claimed in claim 5, wherein the computer program is designed to determine a position and/or dimensions of blood vessels in the target area based on the OCT angiography data, the computing routine of the computer program for determining the target area in the 3-D reconstruction of the object region volume taking account a course and/or the position and/or the dimensions of the blood vessels in the target area.

7. The arrangement as claimed in claim 1, wherein the computer program contains a routine for determining a target area and/or a target position for the item in provided data determined presurgery and has a registration routine for registering the data determined presurgery with the 3-D reconstruction of the object region volume and a transfer routine for transferring the target area and/or the target position in the data determined presurgery to the 3-D reconstruction of the object region volume.

8. The arrangement as claimed in claim 1, wherein the item is a surgical instrument which comprises a capillary with an opening for release of a medium.

9. The arrangement as claimed in claim 8, wherein the computing routine of the computer program serves to determine as a second guide variable a target value for a volume of the released medium by processing the target area in the 3-D reconstruction of the object region volume and/or by processing data determined presurgery and/or by processing OCT scanning information obtained by the OCT device by scanning the object region volume and/or by way of an input of a target value by a surgeon.

10. The arrangement as claimed in claim 8, wherein the computing routine of the computer program serves to determine an actual value of a volume of the medium released into the target area by comparing data of the target area in the 3-D reconstruction of the object region volume and/or scanning information of the target area obtained by the OCT device by scanning the object region volume before and during the release of the medium.

11. The arrangement as claimed in claim 8, wherein the computing routine of the computer program is designed to determine as a second guide variable for a readjustment of a volume of the released medium a difference between a target value and an actual value of the volume of the medium released into the target area.

12. The arrangement as claimed in claim 1, wherein the computing routine of the computer program serves to determine as a second guide variable a position of a substance to be removed and/or an amount of the substance to be removed by processing the target area in the 3-D reconstruction of the object region volume and/or by processing data determined presurgery and/or by way of the input of a target value by a surgeon.

13. The arrangement as claimed in claim 12, wherein a visualization routine for visualizing the position of the substance to be removed and/or the amount of the substance to be removed in the object region volume.

14. A non-transitory computer readable storable medium storing a computer program for determining a 3-D reconstruction of an object region volume in an object region and for determining a relative position of a section of an item in the object region volume by processing optical coherence tomography (OCT) scanning information obtained by an OCT device by scanning the object region volume, the computer program comprising:
   a computing routine for determining a target area in the 3-D reconstruction of the object region volume, and
   a path planning routine that calculates an optimal path of the item to a spatial target position in the target area as a guide variable to guide the item in the object region, the optimal path being calculated based on a criterion, the criterion being a measure of shadowing that quantifies a presence of shadows caused by the item in the 3-D reconstruction.

15. A method for determining a 3-D reconstruction of an object region volume in an object region and for determining a relative position of a section of an item in the object region volume by processing optical coherence tomography (OCT) scanning information obtained by an OCT device by scanning the object region volume, comprising:
   determining a target area in the 3-D reconstruction of the object region volume, and
   calculating an optimal path of the item to a spatial target position in the target area as a guide variable to guide the item in the object region, the optimal path being calculated based on a criterion, the criterion being a measure of shadowing that quantifies a presence of shadows caused by the item in the 3-D reconstruction.

* * * * *